(12) United States Patent
Marsh et al.

(10) Patent No.: US 9,645,012 B2
(45) Date of Patent: May 9, 2017

(54) RAPID AUTOMATED INFRARED THERMOGRAPHY FOR INSPECTING LARGE COMPOSITE STRUCTURES

(71) Applicant: The Boeing Company, Chicago, IL (US)

(72) Inventors: Bobby J. Marsh, Lake Stevens, WA (US); Gary E. Georgeson, Tacoma, WA (US); Jeffrey R. Thompson, Auburn, WA (US)

(73) Assignee: The Boeing Company, Chicago, IL (US)

( * ) Notice: Subject to any disclaimer, the term of this patent is extended or adjusted under 35 U.S.C. 154(b) by 102 days.

(21) Appl. No.: 14/827,788

(22) Filed: Aug. 17, 2015

(65) Prior Publication Data

US 2017/0052070 A1 Feb. 23, 2017

(51) Int. Cl.
| | |
|---|---|
| *G01J 5/10* | (2006.01) |
| *G06T 7/00* | (2017.01) |
| *G01S 17/06* | (2006.01) |
| *G01D 5/347* | (2006.01) |
| *G06T 7/40* | (2017.01) |
| *H04N 5/225* | (2006.01) |

(Continued)

(52) U.S. Cl.
CPC .............. *G01J 5/10* (2013.01); *G01D 5/347* (2013.01); *G01S 17/06* (2013.01); *G06K 9/00671* (2013.01); *G06T 7/0004* (2013.01); *G06T 7/0057* (2013.01); *G06T 7/40* (2013.01); *H04N 5/2256* (2013.01); *H04N 5/247* (2013.01); *H04N 5/332* (2013.01); *G01J 2005/0077* (2013.01); *G01J 2005/0081* (2013.01); *G06T 2207/10048* (2013.01); *G06T 2207/20221* (2013.01); *G06T 2207/30108* (2013.01)

(58) Field of Classification Search
CPC ......... G06T 7/0004; G06T 7/38; G06T 7/521; G06T 7/55; G06T 7/97; G06T 2207/10048; G06T 2207/20221; G06T 2207/30108; G01J 2005/0077; G01J 2005/0081
See application file for complete search history.

(56) References Cited

U.S. PATENT DOCUMENTS

| 6,751,342 B2 | 6/2004 | Shepard ....................... 382/141 |
| 6,826,299 B2 | 11/2004 | Brown et al. ................ 382/154 |

(Continued)

*Primary Examiner* — Andrew W Johns
(74) *Attorney, Agent, or Firm* — Ostrager Chong Flaherty & Broitman P.C.

(57) ABSTRACT

Systems and methods for infrared thermographic inspection of large-scale composite structures such as sections of an aircraft fuselage. Optical metrology is used to precisely locate the infrared images relative to a three-dimensional coordinate system of the composite structure. The optical metrology may comprise laser tracking or photogrammetry or both. In some embodiments, the optical metrology comprises laser tracking merged with photogrammetry. Once the infrared images have been precisely located relative to the coordinate system of the composite structure, structural data about the composite structure (e.g., thickness data) can be retrieved from a database containing a three-dimensional model of the composite structure. In the case of thermographic porosity measurements, the infrared imaging data can be correlated with thickness data to determine the porosity of the composite structure in the inspection area.

15 Claims, 14 Drawing Sheets

(51) Int. Cl.
  *H04N 5/33*   (2006.01)
  *H04N 5/247*  (2006.01)
  *G06K 9/00*   (2006.01)
  *G01J 5/00*       (2006.01)

(56) References Cited

U.S. PATENT DOCUMENTS

| | | | |
|---|---|---|---|
| 6,990,215 B1 | 1/2006 | Brown et al. | 382/106 |
| 7,075,084 B2 | 7/2006 | Thompson et al. | 250/341.6 |
| 7,110,194 B2 | 9/2006 | Hubbs | 359/822 |
| 7,119,338 B2 | 10/2006 | Thompson et al. | 250/341.6 |
| 7,186,981 B2 | 3/2007 | Shepard et al. | 250/341.1 |
| 7,287,902 B2 | 10/2007 | Safai et al. | 374/5 |
| 7,454,265 B2 | 11/2008 | Marsh | 700/195 |
| 7,513,964 B2 | 4/2009 | Ritter et al. | 156/64 |
| 7,587,258 B2 | 9/2009 | Marsh et al. | 700/195 |
| 7,743,660 B2 | 6/2010 | Marsh et al. | 73/633 |
| 7,783,376 B2 | 8/2010 | Marsh et al. | 700/195 |
| 7,800,758 B1 | 9/2010 | Bridges et al. | 356/482 |
| 8,043,033 B2 | 10/2011 | Clark | 408/1 R |
| 8,467,071 B2 | 6/2013 | Steffey et al. | 356/614 |
| 8,713,998 B2 | 5/2014 | Troy et al. | 73/104 |
| 8,892,252 B1 | 11/2014 | Troy et al. | G01B 11/14 |
| 2007/0269098 A1 | 11/2007 | Marsh | 382/141 |
| 2009/0008554 A1* | 1/2009 | Weir et al. | 250/338.1 |
| 2010/0239121 A1* | 9/2010 | Meier | 382/103 |
| 2013/0135480 A1 | 5/2013 | Stratmann et al. | H04N 5/232 |

\* cited by examiner

RAPID AUTOMATED INFRARED THERMOGRAPHY FOR INSPECTING LARGE COMPOSITE STRUCTURES

BACKGROUND

This disclosure generally relates to non-destructive inspection (NDI) of structures and more particularly relates to non-destructive detection of defects in a structure using thermographic image data.

Non-destructive inspection of structures involves thoroughly examining a structure without harming the structure or requiring significant disassembly. Inspection may be performed during manufacturing of a structure and/or after a structure has been put in service to determine the condition, quality, or structural state of the structure.

The production manufacturing of large composite structures for an active airplane program needs to be done at a rate that meets schedule commitments. Non-destructive inspection of primary structure is a necessary part of the manufacturing process and must be done at a rate capable of keeping up with the production schedule.

For example, it is known to fabricate barrel-shaped fuselage sections made of composite material with high throughput. The finished fuselage sections need to undergo NDI also at a high rate. Some existing solutions for inspecting barrel-shaped fuselage sections are large, expensive multiple-axis robotic systems which move ultrasonic transducer arrays over the outer mold line (OML) of the fuselage section using encoded rails and end effectors guided to follow pre-programmed paths.

Active (i.e., pulsed) thermography is another method used in the aerospace and power generation industries to nondestructively evaluate structural components for sub-surface defects. It is effective for uncovering internal bond discontinuities, delaminations, voids, inclusions, and other structural defects that are not detectable by visual inspection of the component.

There is a need for improvements in systems and methods for non-destructive inspection of large structures made of composite material to facilitate a high rate of production.

SUMMARY

The subject matter disclosed herein is directed to systems and methods for rapid infrared thermographic inspection of large structures (e.g., curved cylinder-like workpieces). The systems and methods disclosed herein have particular application in the thermographic inspection of large structures made of composite material (e.g., a composite laminate made of fiber-reinforced plastic). For the sake of illustration, systems and methods for infrared thermographic inspection of barrel-shaped (e.g., half or full barrel) fuselage sections made of composite material will be disclosed in detail. However, it should be appreciated that the apparatus disclosed herein can be employed in the infrared thermographic inspection of large composite structures other than fuselage sections.

In accordance with embodiments disclosed in detail below, the inspection apparatus comprises flash lamps and infrared cameras, which are employed to thermographically inspect large composite structures in a non-contact, non-couplant manner. The flash lamps and infrared cameras may be supported by one or more robots that travel along tracks. As used herein, the term "tracks" encompasses rails, grooves, guide surfaces, and equivalents thereof. A track may be straight (i.e., linear) or curved. In the alternative, the flash lamps and infrared cameras could be mounted on a moving gantry (i.e., a platform that spans the composite structure and travels along parallel tracks).

The infrared imaging data captured by the infrared cameras can be processed to detect internal defects, particularly delaminations and excessive porosity, in composite structures. A computer system can be programmed to locate and quantify those types of flaws based on at least the infrared imaging data. The system can collect inspection data for detecting delaminations and excessive porosity over large surface areas of the composite structure very rapidly.

In the case of porosity measurement using infrared thermography, it is important to know the thickness of the composite part at each measurement point. In one embodiment disclosed in detail below, a laser tracker uses optical targets to tie the location of the composite part to the location of at least one infrared camera directly or, alternatively (and slightly less accurately), through the base of a robot to which the infrared camera is mounted. In another embodiment, the laser tracker uses optical targets to tie the location of the composite part to the location of a pair of photogrammetry cameras. Common targeting for the laser tracker, photogrammetry cameras, and infrared camera locks everything together. A model of the composite part (e.g., provided in the form of a CAD file containing three-dimensional model data), with known thicknesses, is then tied to the infrared thermographic images using the location information acquired by the laser tracker. As a result, every point on the infrared thermographic image has a known thickness that can be used to compute percent porosity. In one implementation, thickness is correlated to porosity by means of correlation curves established with reference standards for respective ranges of porosity and thickness.

One aspect of the subject matter disclosed in detail below is a method for infrared thermographic inspection comprising: (a) moving an infrared camera to a first location whereat a field of view of the infrared camera encompasses a first inspection area of a surface of the composite structure; (b) determining a first coordinate location of the field of view of the infrared camera in a coordinate system of the composite structure using optical metrology while the infrared camera is at the first location; (c) activating at least one flash lamp to output light that illuminates at least portions of the first inspection area; (d) activating the infrared camera to acquire first infrared imaging data while the field of view of the infrared camera encompasses at least the first inspection area; (e) moving the infrared camera to a second location whereat the field of view of the infrared camera encompasses a second inspection area of the surface of the composite structure; (f) determining a second coordinate location of the field of view of the infrared camera in the coordinate system of the composite structure using optical metrology while the infrared camera is at the second location; (g) activating at least one flash lamp to output light that illuminates at least portions of the second inspection area; (h) activating the infrared camera to acquire second infrared imaging data while the field of view of the infrared camera encompasses at least the second inspection area; and (i) stitching the first and second infrared imaging data together based on at least the first and second coordinate locations of the field of view of the infrared camera in the coordinate system of the composite structure. The optical metrology may comprise one of the following: laser tracking, photogrammetry, laser tracking merged with photogrammetry, or laser radar.

In accordance with some embodiments of the method described in the preceding paragraph, steps (b) and (f)

collectively comprise: placing optical targets on the composite structure; directing respective pulses of light from a laser tracker toward the optical targets on the composite structure; processing light returned from the optical targets on the composite structure to the laser tracker to determine first location data representing a coordinate location of the composite structure in a coordinate system of the laser tracker; placing optical targets on a robot base that supports a robotic arm which supports the infrared camera; directing respective pulses of light from the laser tracker toward the optical targets on the robot base; processing light returned from the optical targets on the robot base to the laser tracker to determine second location data representing a coordinate location of the robot base in the coordinate system of the laser tracker; encoding movements of the robotic arm; and computing the first and second coordinate locations of the field of view of the infrared camera in the coordinate system of the composite structure based on at least the first and second location data and encoded movements of the robotic arm.

In accordance with other embodiments of the method described above, steps (b) and (f) collectively comprise: placing optical targets on the composite structure; directing respective pulses of light from the one or more laser trackers toward the optical targets on the composite structure; processing light returned from the optical targets on the composite structure to determine first location data representing a coordinate location of the composite structure in a coordinate system of the one or more laser trackers; attaching respective sets of optical targets to first, second and third bars; placing the first, second and third bars adjacent the composite structure in respective locations so that the first and second bars are separated by the first inspection area, and the second and third bars are separated by the second inspection area; directing respective pulses of light from the one or more laser trackers toward the optical targets on the first and second bars during activations of the infrared camera in step (d); directing respective pulses of light from the one or more laser trackers toward the optical targets on the second and third bars during activations of the infrared camera in step (h); processing light returned from the optical targets on the first, second and third bars to determine second location data representing respective coordinate locations of the first, second and third bars in the coordinate system of the one or more laser trackers; and computing the first and second coordinate locations of the field of view of the infrared camera in the coordinate system of the composite structure based on at least the first and second location data and the first and second infrared imaging data. In at least one embodiment, computing the first and second coordinate locations of the field of view of the infrared camera in the coordinate system of the composite structure comprises identifying portions of the first infrared imaging data which correspond to light returned from the optical targets on the first and second bars.

A further aspect of the subject matter disclosed in detail below is a method for infrared thermographic inspection comprising: (a) attaching a pair of photogrammetry cameras to an infrared camera to form a camera assembly; (b) moving the camera assembly to a first location whereat respective fields of view of the photogrammetry cameras encompass a first inspection area of a surface of the composite structure; (c) determining a first coordinate location of a field of view of the photogrammetry cameras in a coordinate system of the composite structure using optical metrology while the camera assembly is at the first location; (d) activating at least one flash lamp to output light that illuminates at least portions of the first inspection area; (e) activating the infrared camera to acquire first infrared imaging data while the field of view of the infrared camera encompasses at least the first inspection area; (f) activating a projector to project a pattern of light onto the first inspection area while the camera assembly is at the first location; (g) activating the photogrammetry cameras to acquire first photogrammetry data while the field of view of the photogrammetry cameras encompasses at least a portion of the projected pattern of light on the first inspection area; (h) moving the camera assembly to a second location whereat the field of view of the photogrammetry cameras encompasses a second inspection area of the surface of the composite structure; (i) determining a second coordinate location of the field of view of the photogrammetry cameras in the coordinate system of the composite structure using optical metrology while the camera assembly is at the second location; (j) activating at least one flash lamp to output light that illuminates at least portions of the second inspection area; (j) activating the infrared camera to acquire second infrared imaging data while the field of view of the infrared camera encompasses at least the second inspection area; (k) activating a projector to project a pattern of light onto the second inspection area while the camera assembly is at the second location; (l) activating the photogrammetry cameras to acquire second photogrammetry data while the field of view of the photogrammetry cameras encompasses at least a portion of the projected pattern of light on the second inspection area; (m) stitching the first and second photogrammetry data together based on at least the first and second coordinate locations of the field of view of the photogrammetry cameras in the coordinate system of the composite structure; (n) correlating the first and second infrared imaging data to the first and second photogrammetry data respectively; and (o) stitching the first and second infrared imaging data together based on at least the results of steps (m) and (n).

Yet another aspect of the subject matter disclosed in detail below is a method for infrared thermographic inspection comprising: (a) placing an infrared camera at a location where a field of view of the infrared camera encompasses an inspection area of a surface of a composite structure; (b) locating the field of view of the infrared camera in a coordinate system of the composite structure using optical metrology; (c) activating at least one flash lamp to output light that illuminates at least portions of the inspection area; (d) after step (c), activating the infrared camera to acquire infrared imaging data while the field of view of the infrared camera encompasses at least the inspection area; (e) correlating a set of the acquired infrared imaging data with three-dimensional model data representing characteristics of composite structure under the inspection area, the correlating being based on at least the location of the field of view of the infrared camera in the coordinate system of the composite structure; (f) acquiring structural data from the three-dimensional model data, the structural data representing characteristics of the composite structure under the inspection area; (g) correlating the acquired structural data with the set of acquired infrared imaging data; (h) computing values of a parameter indicative of one of the characteristics of the composite structure under the inspection area based on at least the correlated structural data and infrared imaging data; and (i) outputting parameter data representing the computed parameter values. This method may further comprise identifying parameter data that is indicative of a defect. The defect can, for examples, be delamination or porosity that equals or exceeds a specified threshold. In some implementations, the structural data can be thickness data and the parameter can be porosity.

In accordance with some embodiments of the method described in the preceding paragraph, step (h) comprises: selecting a data set from a thermal signature database, the data set representing a multiplicity of thermal signatures of a composite structure having the thickness and different respective porosity percentages; identifying a thermal signature of the multiplicity that best matches a subset of the set of acquired infrared imaging data corresponding to the coordinate position; retrieving from the thermal signature database porosity data associated with the identified thermal signature; and associating the retrieved porosity data with the coordinate position.

Another aspect of the subject matter disclosed in detail below is a system for infrared thermographic inspection of a workpiece, comprising: a robot comprising a movable robot base and an extendible robotic arm having a proximal end coupled to the robot base; a frame mounted to a distal end of the robotic arm; a target projector mounted to the frame; a flash lamp mounted to the frame; and a camera assembly mounted to the frame, the camera assembly comprising first and second camera pairs, the first camera pair comprising a first infrared camera and a first photogrammetry camera, and the second camera pair comprising a second infrared camera and a second photogrammetry camera, wherein the target projector and the flash lamp are disposed between the first and second camera pairs. This system may further comprise a laser tracker, a first set of at least three optical targets attached to the first camera pair, a second set of at least three optical targets attached to the second camera pair, and a computer system configured to stitch first and second infrared imaging data acquired by the infrared camera based on at least location data acquired by the laser tracker and photogrammetry data acquired by the first and second photogrammetry cameras.

Other aspects of systems and methods for infrared imaging of large composite structures are disclosed below.

BRIEF DESCRIPTION OF THE DRAWINGS

Reference will hereinafter be made to the drawings in which similar elements in different drawings bear the same reference numerals.

DETAILED DESCRIPTION

Figure 1:
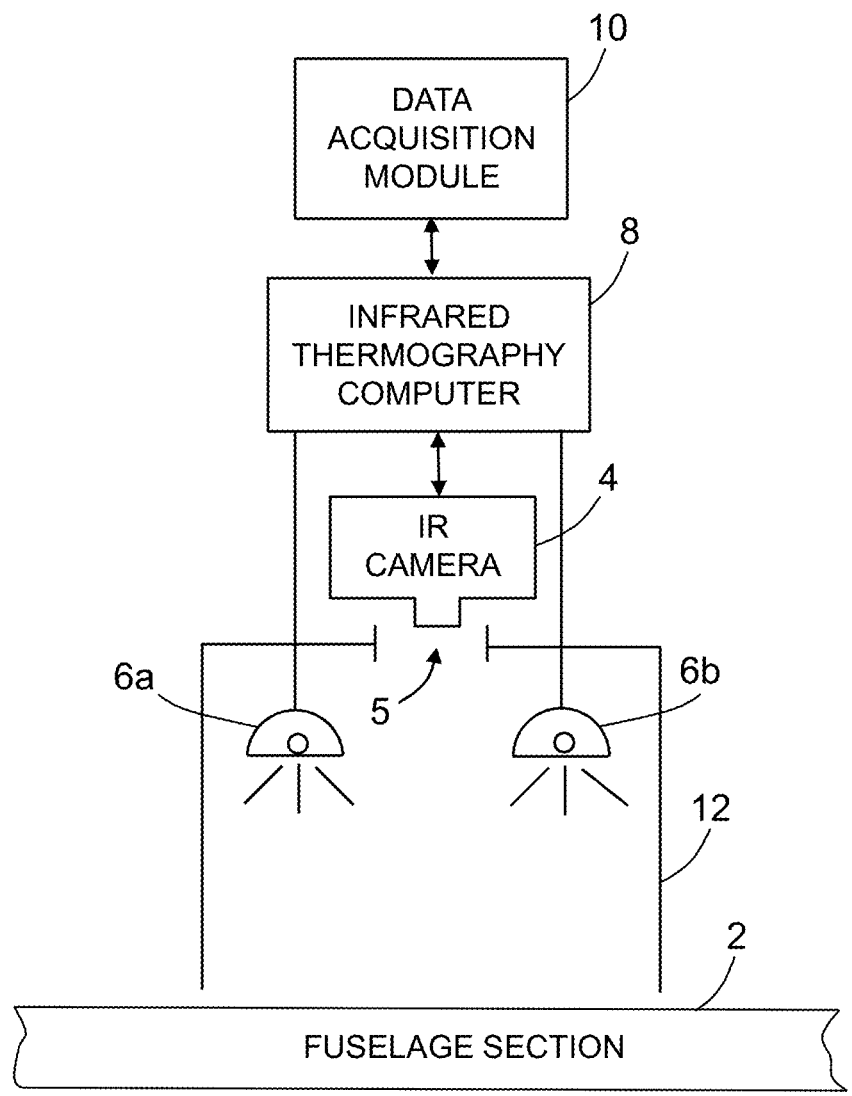
FIG. 1 is a block diagram identifying some components of a system for thermographic imaging of a fuselage section.

For the purpose of illustration, location calibration for robotic thermographic inspection of structures in the form of curved cylinder-like workpieces (such as half- or full-barrel-shaped sections of an aircraft fuselage) made of composite material will be described. However, it should be appreciated that the calibration processes disclosed in detail below may also be used in connection with composite structures having geometries which are not curved and cylinder-like.

Infrared thermography methods and devices make it possible to perform non-destructive testing of a material to detect defects, variations in the properties of the material, or differences in thickness of a coating or layer of the material. Infrared imaging can detect local variations in thermal diffusivity or thermal conductivity at or beneath the surface of the material. Infrared thermography can be used on metals, such as ferrous materials, including steel, or on non-metallic materials, such as plastics, ceramics, or composite materials.

Active thermography is used to nondestructively evaluate samples for sub-surface defects. It is effective for uncovering internal bond discontinuities, delaminations, voids, inclusions, and other structural defects that are not detectable by visual inspection of the sample. Generally, active thermography involves heating or cooling the sample to create a difference between the sample temperature and the ambient temperature and then observing the infrared thermal signature that emanates from the sample as its temperature returns to ambient temperature. An infrared camera is used because it is capable of detecting any anomalies in the cooling behavior, which would be caused by sub-surface defects blocking the diffusion of heat from the sample surface to the sample's interior. More particularly, these defects cause the surface immediately above the defect to cool at a different rate than the surrounding defect-free areas.

As the sample cools, the infrared camera monitors and records an image time sequence indicating the surface temperature, thereby creating a record of the changes in the surface temperature over time.

Typically, the surface of the material is heated using a flash lamp and after a fixed period of time, a thermal image is taken of the surface of the heated material. Systems for thermographic heating typically employ xenon flashtubes and off-the-shelf photographic power supplies for sample excitation. An infrared camera images the infrared spectral radiance from the surface of the material, which is representative of the temperature of the surface of the material. Differences in temperature of the surface of the material indicate differing thermal characteristics of the material. These variations in thermal characteristics of the material indicate a possible material defect or the inclusion of a foreign material.

Structural thickness and stack-up geometry needed for infrared signature processing is obtained by knowing the exact location of the infrared camera's field of view on the surface of the fuselage section.

FIG. 1 is a block diagram identifying some components of a system for thermographic imaging of a fuselage section 2. This infrared thermographic inspection system comprises a digital infrared camera 4 having a lens that is directed through a camera lens aperture 5 in a hood 12, which is designed to form a hooded enclosure adjacent to the surface being inspected. A pair of flash lamps 6a and 6b are disposed inside and in fixed spatial relationship to the hood 12. The flash lamps 6a and 6b produce flashes of light in response to trigger signals from an infrared thermography computer 8, which also controls operation of the infrared camera 4. One example of a type of infrared camera 4 suitable for use with at least some of the embodiments disclosed herein includes a focal plane array (FPA) device configured to act as a spectral radiometer. Further details concerning other components that may be included in a flash lamp assembly of a type comprising an infrared camera, a pair of flash lamps and a hood can be found, for example, in U.S. Pat. No. 7,186,981.

In accordance with one method of thermographic inspection, first the flash lamps 6a and 6b are triggered to transfer heat to the composite material of the fuselage section 2. Preferably, during cooling of the composite material, the infrared camera 4 is triggered periodically to capture successive digital images of the varying spectral radiance of the heated portion of the fuselage section 2. Preferably, the thermally excited (heated) region of the composite material being inspected will cool monotonically after the excitation source removed until the sample reaches thermal equilibrium with its surroundings. The thermal response of any point on the surface of the composite material during the time interval immediately after heating will decay in such a manner that the natural logarithm of the temperature-time response of a defect-free sample, as it cools, is a function that can be approximated by a straight line.

The digital infrared imaging data captured by infrared camera 4 is received by the infrared thermography computer 8 for processing. The infrared thermography computer 8 is programmed to process infrared imaging data to detect and locate material edges, foreign objects under the surface of the material, or other material anomalies, such as delaminations and out-of-tolerance porosity. The infrared imaging data may be displayed on a display monitor (not shown in FIG. 1), which may be integrated with or separate from infrared thermography computer 8.

In accordance with the embodiment depicted in FIG. 1, the infrared thermography computer 8 may have digital image acquisition capabilities to convert the infrared imaging data from the infrared camera 4 to a format that can be analyzed and mathematically manipulated by the infrared thermography computer 8. An optional data acquisition module 10 may be incorporated in or separate from (as depicted in FIG. 1) the infrared thermography computer 8. The data acquisition module 10 may be used if the infrared camera 4 captures multiple spatially different images to generate a complete mosaic image of the surface of the composite structure when the latter is too large to fit in a single image frame. The infrared thermography computer 8 may be further programmed to analyze the infrared imaging data captured by the infrared camera 4. In particular, the time history of the surface temperature response of the fuselage section 2 as it returns to room temperature can be analyzed to detect the presence of defects in the composite material.

In the context of the specific application of inspecting fuselage sections, a non-destructive inspection system may comprise means for scanning the skin of the fuselage section from a vantage point external to the fuselage section and means for scanning substructure, such as stiffeners attached to the inside of the fuselage section. The means for scanning stiffeners on the inside of a fuselage section can work in concert and concurrently with the means that scan the fuselage section externally. In the alternative, the external and internal scanning can be performed at different times and/or at different places. The fuselage sections can be scanned externally before or after the stiffeners have been attached. In the embodiments disclosed below, the internal scanning means comprise ultrasonic transducer arrays, while the external scanning means comprise infrared cameras.

Figure 2:
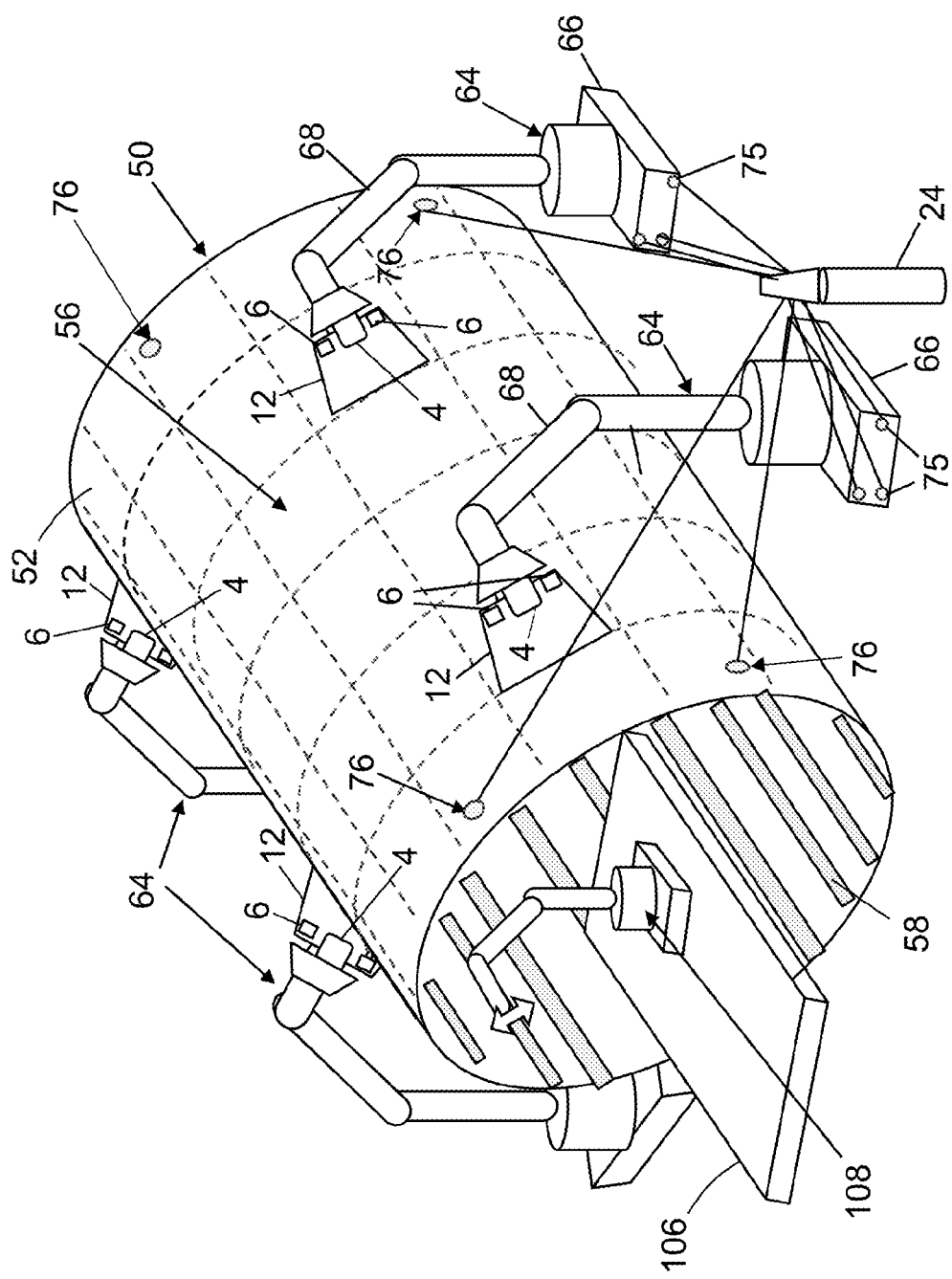
FIG. 2 is a diagram representing an isometric view of a full-barrel fuselage section being inspected by an infrared thermographic inspection system having multiple robots in accordance with one embodiment. A laser tracker determines the locations of the robots relative to the fuselage section using optical targets attached to the fuselage section and to the robot bases.

FIG. 2 depicts a full-barrel fuselage section 50 being inspected by a non-destructive inspection system comprising multiple robots 64 equipped with infrared thermography assemblies in accordance with one embodiment. Each robot 64 comprises a movable robot base 66 and an articulated robotic arm 68 having a proximal end coupled to the robot base 66. Each robot base 66 may be mounted to a mobile holonomic crawler vehicle or coupled to a linear track (not shown in FIG. 2). A respective infrared thermography assembly is coupled to a distal end of each robotic arm 68. Each infrared thermography assembly comprises an infrared camera 4 and two or more flash lamps 6 attached inside a hood 12. Each hood 12 may be sized to cover a respective square area 56 on the outer surface 52 of the fuselage section 50. The infrared imaging data acquired from adjacent square areas 56 can be stitched together based on measurements of the respective locations of the robot base 66 using a laser tracker 24 and respective movements of the robotic arms 68 using encoders incorporated in the robot 64. The stitching 60 process may be performed on a real-time basis or may be performed at a later time. In addition, the non-destructive inspection system depicted in FIG. 2 may comprise a robot 108 movable on a platform 106 for ultrasonic inspection of stiffeners 58 attached to the internal surface of the fuselage section 50.

In accordance with one embodiment, a laser tracker 24 is used to determine the locations of the robot bases 66 relative to the fuselage section 50. This is accomplished using optical targets 75 attached to the robot bases 66 and optical targets 76 attached to the fuselage section 50. Optical targets 76 may comprise spherically mounted retroreflectors, which will be described in more detail below. The optical targets 76 may be inserted in holes formed at predetermined locations about the outer surface 52 of the fuselage section 50. The holes in the fuselage section 50 may be components of a part reference system, such as a determinant assembly coordinate system, in which parts are referenced to each other (as opposed to the parts being referenced to assembly tooling). The part reference system suitably indexes the location of each of the holes in three dimensions.

Figure 3:
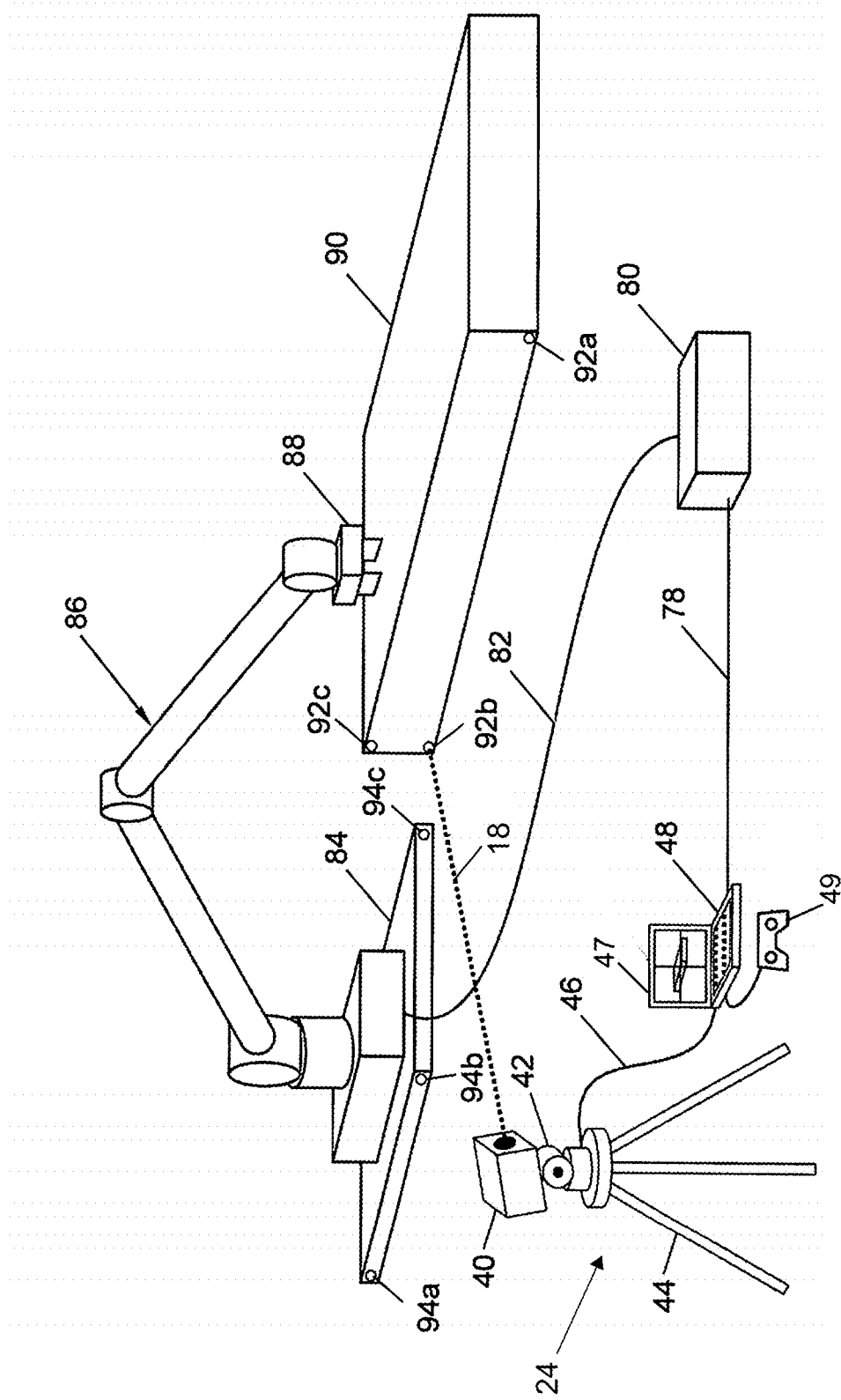
FIG. 3 is a diagram representing an isometric view of a physical setup in which a laser tracker is aimed at a robotic workcell with multiple moving objects.

FIG. 3 is an isometric view of components of a system having automated apparatus for performing non-destructive inspection and means for calibrating the location of a workpiece relative to the automated apparatus. In the embodiment depicted in FIG. 3, the means for calibrating is a laser tracker 24 comprising a video camera 40 and a laser range meter (not shown) on a controllable pan-tilt mechanism 42 mounted on a tripod 44. The video camera 40 and pan-tilt mechanism 42 are operated by a laser tracking computer 48. The laser tracking computer 48 communicates with the video camera 40, laser range meter, and the pan-tilt mechanism 42 through a video/control cable 46. The pan and tilt angles of the pan-tilt mechanism 42 and, therefore, the orientation of the video camera 40 can be controlled using the keyboard of the computer or some other input device, such as the gamepad interface 49 shown in FIG. 3. The optical image field, with crosshair overlay, as sighted by the video camera 40, can be displayed on the monitor 47 of the laser tracking computer 48.

The laser tracker 20 seen in FIG. 3 can be used to determine the offset of the part 90 (e.g., a fuselage section) relative to the robot base 84. The robot controller 80 controls the robot, the location of the robot base 84, and the location of the end effector 88 in a workcell frame of reference. The laser tracking computer 48 communicates with the robot controller 80 through an electrical cable 78. The robot controller 80 is preferably a computer programmed with motion control software for controlling the motion of the end effector 88 relative to the part 90. The motion control commands are sent to a processor (not shown) inside the robot base 84 via an electrical cable 82. Alternatively, wireless communication can be employed.

The location offset between robot base 84 and part 90 (i.e., the location of the coordinate system of the part 90 relative to the coordinate system of the robot) can be determined in a well-known manner. First, the laser tracking computer 48 determines the X, Y, Z values for measured passive target markers 92a-92c placed on the part 90 and the X, Y, Z values for measured passive target markers 94a-94c placed on the robot base 84 when robot base 84 and part 90 2 are at their respective initial locations. This is accomplished by aiming a laser beam 18 at each passive target marker in succession while the laser tracker 20 is in the same location, and recording the distance, pan, and tilt values for each point, and then computing the corresponding X, Y, Z values in the target coordinate system. The laser tracking computer 48 then uses a relative localization process to produce data representing the location of the part 90 relative to the robot base 84. This methodology can be used at the start of each work sequence to establish the relative locations of the robot base 84 and the workpiece 90 to be inspected. This data is output to the robot controller 80 via cable 78.

The foregoing methodology can be used at the start of each work sequence to establish the relative positions of the robot base 84 and the part 90. The robot controller 80 will be able to compute the position and orientation of the end effector 88 relative to the robot base 84 using encoders that encode movements of the articulated robotic arm 86 and kinematics data.

Figure 4:
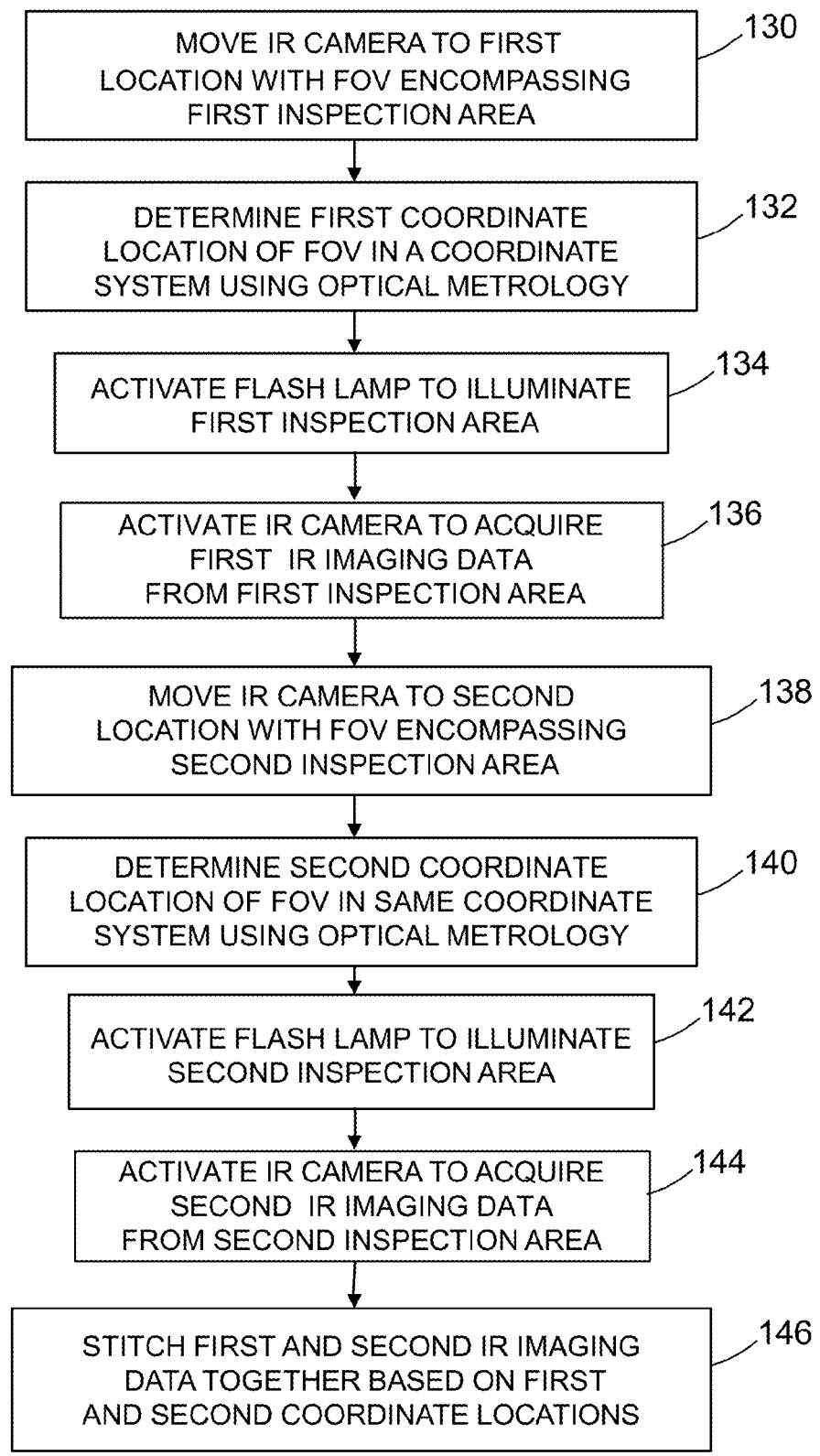
FIG. 4 is a flowchart identifying steps of a method for infrared thermographic inspection in accordance with some embodiments.

FIG. 4 is a flowchart identifying steps of a method for infrared thermographic inspection in which the infrared imaging data captured by an infrared camera at adjacent locations is stitched together. In accordance with the embodiment depicted in FIGS. 2 and 3, the method comprises the following steps: (a) moving an infrared (IR) camera 4 to a first location whereat a field of view (FOV) of the infrared camera 4 encompasses a first inspection area of a surface of the composite fuselage section 50 (step 130); (b) determining a first coordinate location of the field of view of the infrared camera 4 in a coordinate system of the composite fuselage section 50 using optical metrology while the infrared camera 4 is at the first location (step 132); (c) activating at least one flash lamp 6 to output light that illuminates at least portions of the first inspection area (step 134); (d) activating the infrared camera 4 to acquire first infrared imaging data while the field of view of the infrared camera 4 encompasses at least the first inspection area (step 136); (e) moving the infrared camera 4 to a second location whereat the field of view of the infrared camera 4 encompasses a second inspection area of the surface of the composite fuselage section 50 (step 138); (f) determining a second coordinate location of the field of view of the infrared camera 4 in the coordinate system of the composite fuselage section 50 using optical metrology while the infrared camera 4 is at the second location (step 140); (g) activating at least one flash lamp 6 to output light that illuminates at least portions of the second inspection area (step 142); (h) activating the infrared camera 4 to acquire second infrared imaging data while the field of view of the infrared camera 4 encompasses at least the second inspection area (step 144); and (i) stitching the first and second infrared imaging data together based on at least the first and second coordinate locations of the field of view of the infrared camera 4 in the coordinate system of the composite fuselage section 50 (step 146). The optical metrology may comprise laser tracking (as depicted in FIG. 2), photogrammetry (not shown in FIG. 2), or laser radar (not shown in the drawings).

It should be appreciated that the system depicted in FIG. 2 can locate and acquire infrared imaging data in sequence or concurrently.

In accordance with further aspects of the system depicted in FIG. 2 and the method depicted in FIG. 4, the steps of determining the first and second coordinate locations of the field of view of an infrared camera 4 during the capture of adjacent first and second infrared images collectively may comprise the following steps: (a) placing optical targets 76 on the fuselage section 50; (b) directing respective pulses of light from the laser tracker 24 toward the optical targets 76; (c) processing light returned from the optical targets 76 to the laser tracker 24 to determine first location data representing a coordinate location of the fuselage section 50 in a coordinate system of the laser tracker 24; (d) placing optical targets 75 on a robot base 66 that supports a robotic arm 68, which in turn supports the infrared camera 4; (e) directing respective pulses of light from the laser tracker 24 toward the optical targets 75 on the robot base 66; (f) processing light returned from the optical targets 75 to the laser tracker 24 to determine second location data representing a coordinate location of the robot base 66 in the coordinate system of the laser tracker 24; (g) encoding movements of the robotic arm 68; and (h) computing the first and second coordinate locations of the field of view of the infrared camera 4 in the coordinate system of the fuselage section 50 based on at least the first and second location data and encoded movements of the robotic arm 68.

Figure 5:
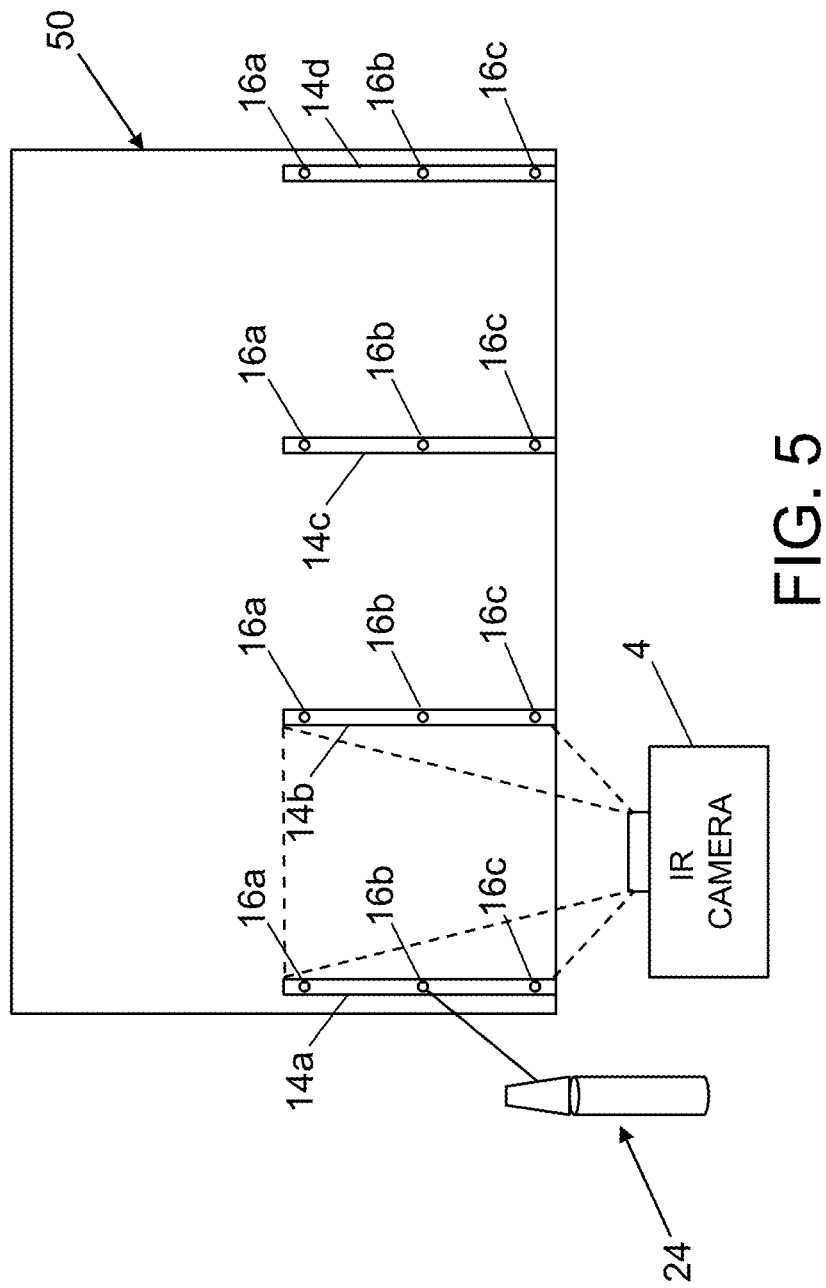
FIG. 5 is a hybrid diagram showing an infrared camera having a field of view that encompasses an area between adjacent vertical bars arranged in front of a full-barrel fuselage section in accordance with an alternative embodiment. A laser tracker determines the locations of the vertical bars relative to the fuselage section using optical targets attached to the fuselage section and to the vertical bars.

FIG. 5 is a hybrid diagram showing a physical setup for an infrared thermographic inspection system in accordance with an alternative embodiment. A plurality of vertical bars 14a-14d are arranged in front of a full-barrel fuselage section 50. The vertical bars 14a-14d are preferably arranged with constant spacing between adjacent vertical bars. Although FIG. 5 shows four vertical bars 14a-14d, three or more vertical bars can be used depending on the length of the fuselage section being inspected. Each vertical bar has three or more well-spaced optical targets attached thereto. In the scenario depicted in FIG. 5, each vertical bar 14a-14d has a respective set of optical targets 16a-16c (e.g., spherically mounted retroreflectors) attached to and spaced apart along each vertical bar. A laser tracker 24 is used to determine the locations of two or more optical targets 16a-16c on each vertical bar 14a-14d relative to the fuselage section 50.

Still referring to FIG. 5, initially an infrared camera 4 is set up so that its field of view encompasses at least an area between adjacent vertical bars 14a and 14b. For the purpose of illustration, it may be assumed that each area between adjacent vertical bars 14a-14d is a respective 6-foot by 6-foot square. First, the laser tracker 24 transmits pulses of coherent light aimed at optical targets attached to the fuselage section (not shown in FIG. 5, but see optical targets 76 in FIG. 2). In accordance with one implementation, the laser tracker transmits pulses of coherent light aimed at two of the three optical targets 16a-16c attached to and spaced apart along each vertical bar on opposite sides of the area being inspected. The light reflected back to the laser tracker 24 from the optical targets is processed to determine the locations of those optical targets in the coordinate system of the fuselage section 50. In this example, the laser tracker 24 is triggered four times. For example, the laser tracker 24 may transmit four pulses of coherent light: two respectively aimed at optical targets 16a and 16c on vertical bar 14a and two respectively aimed at optical targets 16a and 16c on vertical bar 14b. The infrared camera 4 is triggered each time the laser tracker 24 is triggered. For example, the infrared camera 4 will capture a first infrared image when light from the laser tracker 24 impinges on optical target 16a attached to vertical bar 14a, a second infrared image when light from the laser tracker 24 impinges on optical target 16c attached to vertical bar 14a, a third infrared image when light from the laser tracker 24 impinges on optical target 16a attached to vertical bar 14b, and a fourth infrared image when light from the laser tracker 24 impinges on optical target 16c attached to vertical bar 14b. These four infrared images are then precisely located relative to the coordinate system of the fuselage section 50 (since the locations of those optical targets are known) and merged together.

More specifically, an infrared thermography computer (not shown in FIG. 5) may be programmed with software that allows each infrared image to be precisely located in the coordinate system of the fuselage section 50 based on the appearance of hot spots in the infrared image due to the heat produced in an optical target when a pulse of coherent light impinges thereon. For example, SpatialAnalyzer® metrology software (commercially available from New River Kinematics) can be used to correlate the hot spots in an infrared image with the measured locations of the corresponding heated optical targets that produced those hot spots.

After the area between vertical bars 14a and 14b has been imaged by the infrared camera 4, the latter is moved so that its field of view encompasses an area between adjacent vertical bars 14b and 14c. Then the laser tracker is triggered to transmit pulses of coherent light aimed at optical targets 16a and 16b attached to vertical bar 14b and optical targets 16a and 16b attached to vertical bar 14c disposed on opposite sides of the area being inspected. Again the light reflected back to the laser tracker 24 from the optical targets is processed to determine the locations of those optical targets in the coordinate system of the fuselage section 50. Again the infrared camera 4 is triggered each time the laser tracker is triggered. For example, the infrared camera 4 will capture a fifth infrared image when light from the laser tracker 24 impinges on optical target 16a attached to vertical bar 14b, a sixth infrared image when light from the laser tracker 24 impinges on optical target 16c attached to vertical bar 14b, a seventh infrared image when light from the laser tracker 24 impinges on optical target 16a attached to vertical bar 14c, and an eighth infrared image when light from the laser tracker 24 impinges on optical target 16c attached to vertical bar 14c. These four infrared images are then precisely located relative to the coordinate system of the fuselage section 50 and merged together in the manner previously described. Then the infrared images resulting from the merger of the first through fourth infrared images and the merger of the fifth through eighth infrared images can be stitched together.

It should be appreciated that the number of times that the infrared camera 4 is triggered for each 6-foot by 6-foot square area will vary depending on the number of optical targets on an adjacent pair of vertical bars being heated by the laser tracker.

Furthermore, it should also be appreciated that the number of times that the infrared camera 4 is triggered for each 6-foot by 6-foot square area will vary depending on the number of laser trackers being used. If four laser trackers were aimed at respective optical targets and triggered simultaneously, then the infrared camera could be triggered just once, thereby rendering the merger of multiple infrared images for each inspection area unnecessary.

In accordance with one implementation, the vertical bars 14a-14c can be placed a specified distance away from the outer surface or outer mold line (OML) of the fuselage section, while the infrared camera is located so that its respective field of views from adjacent locations will overlap on the strip of OML surface area behind each vertical bar to provide 100% fuselage image capture coverage. The two "angled" image captures will have an overlap in coverage shots, thereby eliminating any "voids" behind the vertical bars 14a-14c. A laser tracker 24 can be used to shoot the optical targets on the vertical bars before the infrared camera shots are taken. Then when the actual survey is done, the laser tracker can confirm the vertical bar locations in every shot taken, thereby providing automatic location confirmation.

Figure 6:
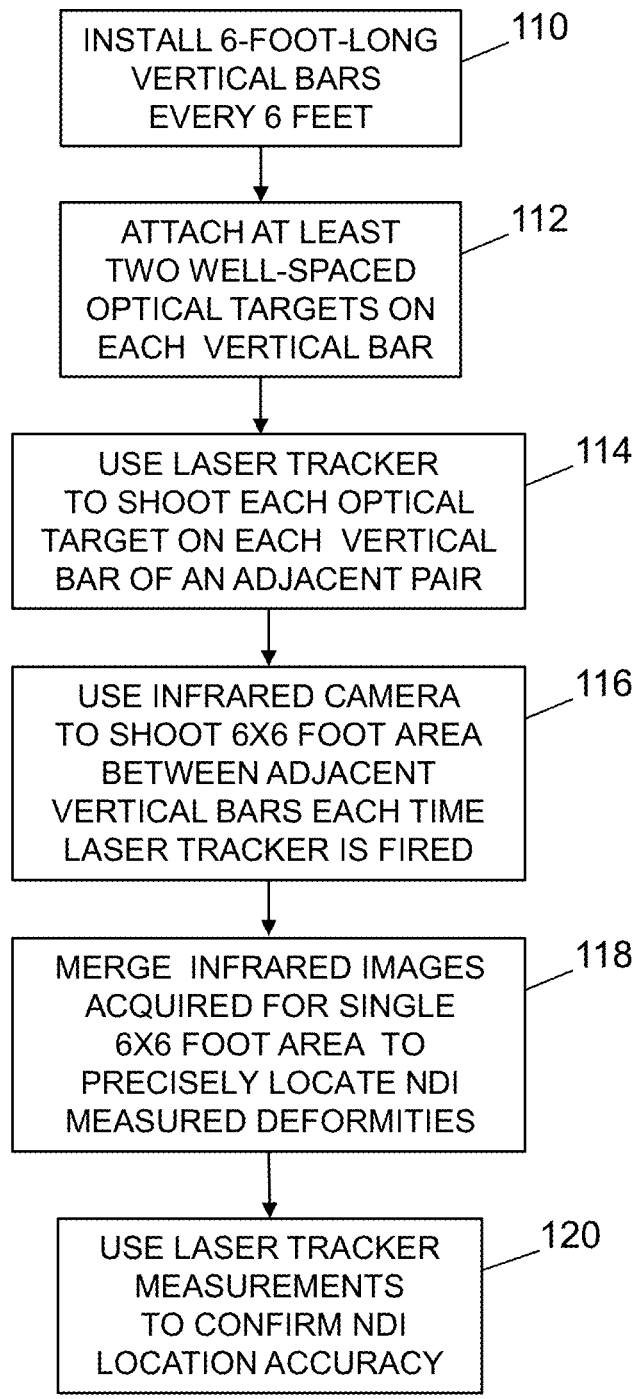
FIG. 6 is a flowchart identifying some steps of a method for thermographically inspecting an area between a pair of spaced vertical bars.

Use of the laser tracker and optical targets enables the field of view of the infrared camera to be determined regardless of the camera-to-part separation distance. This serves to calibrate the field of view so that defect and field of view dimensions are accurately determined for all infrared camera placements FIG. 6 is a flowchart identifying some steps of a method for thermographically inspecting an area between a pair of spaced vertical bars. First, a plurality of 6-foot-long vertical bars are spaced at 6-foot intervals in front of a fuselage section to be inspected (step 110). To confirm stability, the vertical bars can be vacuum attached to the fuselage section. Then at least two well-spaced optical targets are magnetically attached to each vertical bar (step 112). Then the laser tracker (positioned behind and above the infrared camera) is used to shoot each optical target on each vertical bar of an adjacent pair of vertical bars (step 114). The infrared camera is triggered to shoot the 6-foot by 6-foot square area between the adjacent vertical bars each time the laser tracker is fired (step 116). Then the infrared images acquired for a single 6-foot by 6-foot square area are merged to precisely locate NDI measured deformities or defects (step 118). The laser tracker measurements are used to confirm NDI location accuracy (step 120).

The method previously described with reference to FIG. 4 has equal application to the infrared thermographic inspection system partly depicted in FIG. 5. In accordance with further aspects of the system partly depicted in FIG. 5 and the method depicted in FIG. 4, the steps of determining the first and second coordinate locations of the field of view of an infrared camera 4 during the capture of adjacent first and second infrared images collectively comprise the following steps: (a) placing optical targets on the composite structure; (b) directing respective pulses of light from the one or more laser trackers 24 toward the optical targets on the fuselage section 50; (c) processing light returned from the optical targets on the fuselage section 50 to determine first location data representing a coordinate location of the fuselage section 50 in a coordinate system of the one or more laser trackers 24; (d) attaching respective sets of optical targets to first, second and third vertical bars 14a-14c; (e) placing the first, second and third vertical bars 14a-14c adjacent the fuselage section 50 in respective locations so that the first and second vertical bars 14a and 14b are separated by the first inspection area, and the second and third vertical bars 14b and 14c are separated by the second inspection area; (f) directing respective pulses of light from the one or more laser trackers 24 toward the optical targets on the first and second vertical bars 14a and 14b during some activations of the infrared camera; (g) directing respective pulses of light from the one or more laser trackers 24 toward the optical targets on the second and third vertical bars 14b and 14c during other activations of the infrared camera; (h) processing light returned from the optical targets on the first, second and third vertical bars 14a-14c to determine second location data representing respective coordinate locations of the first, second and third vertical bars 14a-14c in the coordinate system of the one or more laser trackers 24; and (i) computing the first and second coordinate locations of the field of view of the infrared camera 24 in the coordinate system of the fuselage section 50 based on at least the first and second location data and the first and second infrared imaging data. In accordance with one embodiment, computing the first coordinate location of the field of view of the infrared camera 24 in the coordinate system of the fuselage section 50 comprises identifying portions of the first infrared imaging data which correspond to light returned from the optical targets on the first and second vertical bars 14a and 14b, while computing the second coordinate location of the field of view of the infrared camera 24 in the coordinate system of the fuselage section 50 comprises identifying portions of the second infrared imaging data which correspond to light returned from the optical targets on the second and third vertical bars 14b and 14c.

In accordance with other embodiments, the laser tracker can use optical targets to tie the location of the composite part to the location of a pair of photogrammetry cameras which are attached to respective infrared cameras. Common targeting for the laser tracker, photogrammetry cameras, and infrared cameras locks everything together. Before describing one embodiment that combines infrared thermography with photogrammetry, it would be helpful to first describe the structure and functionality of a photogrammetry system which is suitable for measuring the outer surface of a fuselage section 50.

Figure 7:
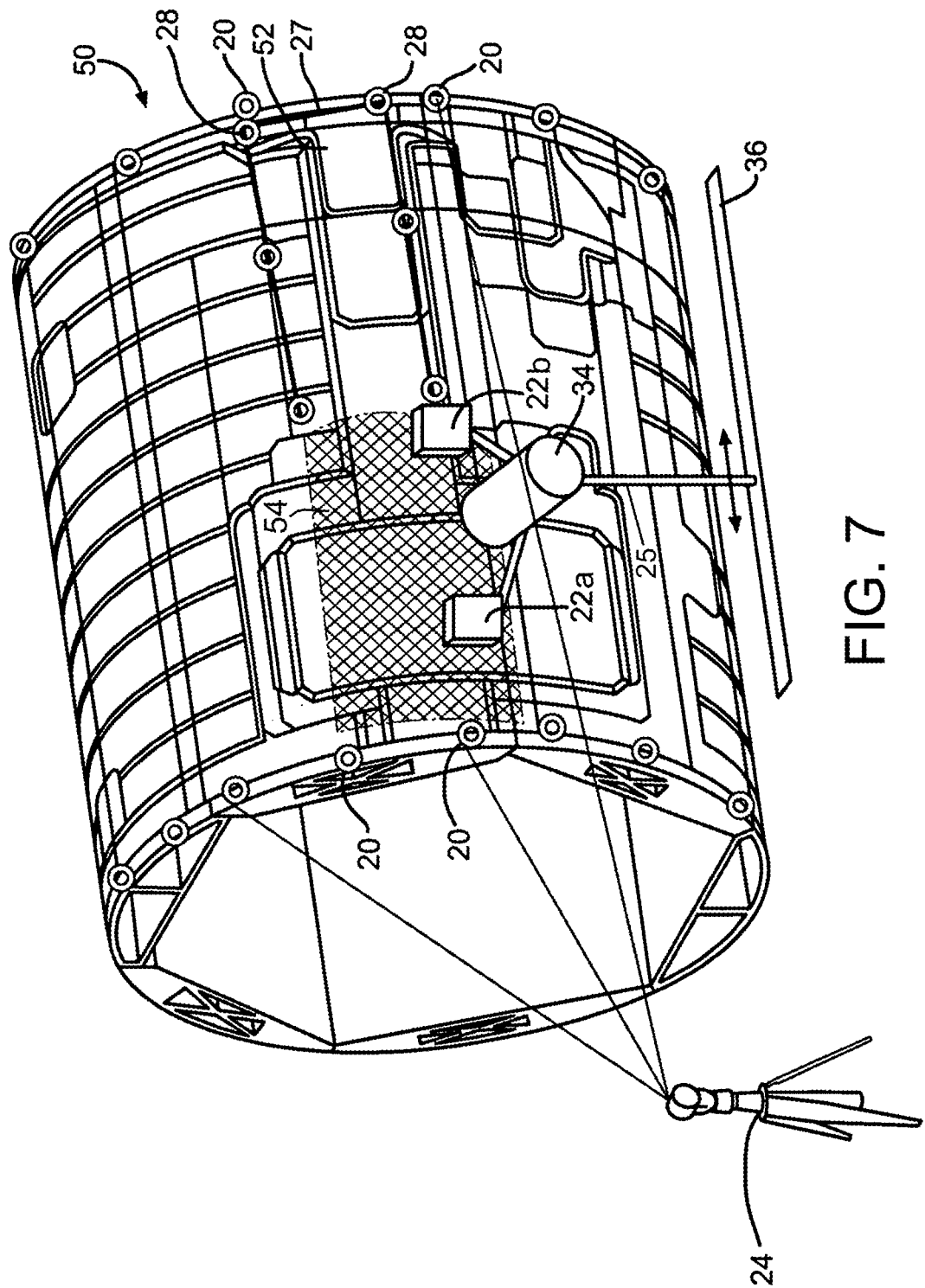
FIG. 7 is a diagram representing an isometric view of a mandrel assembly/fuselage section arrangement with a laser tracker and two photogrammetry cameras for measuring the surface of the fuselage section.

FIG. 7 is a diagram representing an isometric view of a mandrel assembly/fuselage section arrangement with a laser tracker 24 and two photogrammetry cameras 22a and 22b for measuring the surface of the fuselage section 50. FIG. 7 depicts a fully cured full-barrel fuselage section 50 disposed over the outer surface of a mandrel assembly.

As shown in FIG. 7, a multiplicity of optical targets 20 are installed on the outer surface 52 of the fuselage section 50. Respective pluralities of optical targets 20 are installed in respective pluralities of holes at the forward and aft portions of the fuselage section 50. Each of the optical targets 20 may have reflectors which are adapted to reflect photogrammetry pulses of light, and separate reflectors which are adapted to reflect laser beams emitted from laser tracking devices. The optical targets 20 may comprise any of the embodiments disclosed in U.S. Patent Application Publ. No. 2007/0269098 A1, the disclosure of which is hereby incorporated by reference herein in its entirety. In other embodiments, the optical targets 20 may be in any size, type, shape, configuration, orientation, and/or location. The locations (in 3-D coordinate space) of each of the optical targets 20 can be concurrently measured using photogrammetry and laser tracking.

Figure 8:
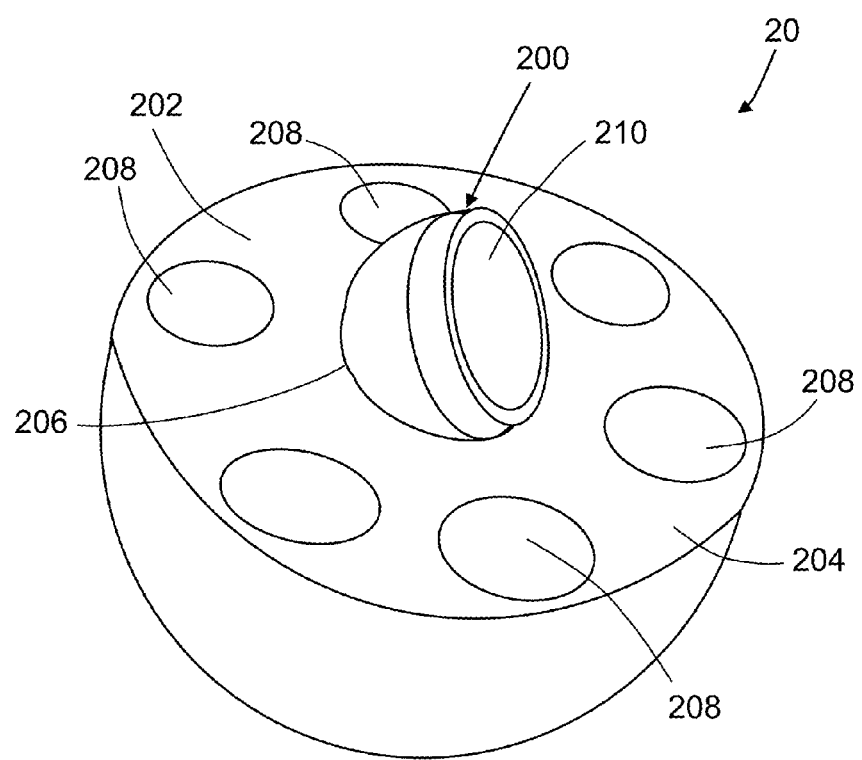
FIG. 8 a diagram representing an isometric view of a combination laser and photogrammetry target.

In accordance with one embodiment depicted in FIG. 8, each optical target 20 may comprise a combination laser tracking and photogrammetry target of the type depicted in FIG. 8. This optical target 20 comprises a retroreflector assembly 200 (commonly referred to as a "spherically mounted retroreflector") which is spherically mounted in a recessed conical nest 206 formed in a hemispherical extended sphere mount 204. Preferably the recessed conical nest 206 is located at the center of extended sphere mount 204. The recessed conical nest 206 holds and locates the hollow stainless steel ball 202 with the aid of a magnet.

The retroreflector assembly 200 comprises a plurality of retroreflectors (not shown in FIG. 8) centrally mounted in a hollow stainless steel ball 202. The hollow stainless steel ball 202 has a circular opening or aperture 210 through which laser light enters the ball and is reflected back along an incident angle to the source by the internally mounted retroreflector. The planar annular upper surface of the extended sphere mount 204 supports a plurality of retroreflective surfaces 208 distributed at equal angular intervals thereon, which surround the recessed conical nest 206. The spherically mounted retroreflector is intended to reflect a pulse of coherent light produced by a laser tracker, while retroreflective surfaces 208 reflect light used in the photogrammetry process.

Returning attention to FIG. 7, the outer surface 52 of the fuselage section 50 can be measured utilizing the photogrammetry and laser tracking procedure described in detail in U.S. Pat. No. 7,454,265, the disclosure of which is hereby incorporated by reference herein in its entirety. As shown in FIG. 7, two photogrammetry cameras 22a and 22b and a laser tracker 24 may be utilized to measure the outer surface 52 of the fuselage section 50 by concurrently measuring the locations of three or more optical targets 20 utilizing both photogrammetry and laser tracking.

The laser tracking measurements may be taken by emitting successive laser beams from the laser tracker 24 towards the outer surface 52 of the fuselage section 50. The laser beams may be reflected off the laser reflectors of one or more of the optical targets 20 back towards the laser tracker 24. The laser tracking data acquired by the laser tracker can be processed to measure one or more target locations in an X, Y, Z coordinate system based on the properties and timing of the returned light using a triangulation technique.

Concurrent with the laser tracking procedure, photogrammetry measurements may be taken by projecting dot patterns of light onto the outer surface 52 and the optical targets 20 using a target projector 34. The target projector 34 is preferably a non-contact 3-D point cloud measurement system that is capable of projecting a dense array of high-contrast targets, such as tens of thousands of dots, onto the outer surface 52 of the fuselage section 50. Some of the projected light can be reflected off the photogrammetry reflectors of multiple optical targets 20 back towards the photogrammetry cameras 22a and 22b. The acquired photogrammetry data is then processed by a photogrammetry computer (not shown in FIG. 7), which computes target locations in an X, Y, Z coordinate system based on at least the properties and timing of the returned light.

A suitable target projector is the PRO-SPOT target projection system, which is commercially available from Geodetic Systems, Inc. The photogrammetry cameras 22a and 22b may be high-speed, high-resolution digital cameras, such as V-STARS M cameras, which are also commercially available from Geodetic Systems, Inc. The two photogrammetry cameras 22a and 22b and the target projector 34 may be attached to a frame, which frame may in turn be attached to a distal end of an articulated robotic arm of a robot (not shown in FIG. 7). The robot may be movable (as indicated by the double-headed arrow in FIG. 7) along a linear track 36 that extends the full length of the fuselage section 50.

In accordance with one proposed implementation, the laser tracker 24 can measure the locations of three or more optical targets at the forward portion of the fuselage section 52 being measured, the locations of three or more optical targets at the aft portion of the fuselage section 52, and the locations of a plurality (e.g., 10) of optical targets 28 distributed around a rectangular frame 27, only the right half of which is shown in FIG. 7. Vertical bars of the type depicted in FIG. 4 can be used in place of the frame 27. Concurrently, the target projector 34 emits a dense array of dots onto an area 54 indicated by hatching in FIG. 7. The two photogrammetry cameras 22a and 22b record a combined digital image covering the area 54 within the frame 27. The combined photogrammetry image shows the positioning of the hundreds of dots on the outer surface 52 of the fuselage section 50. The photogrammetry imaging data indicative of the optical targets 20 can be correlated with the laser tracking data acquired for the same optical targets. As a result, the surface of the fuselage section in area 54 can be measured at points which are precisely located in the frame of reference (i.e., 3-D coordinate system) of the fuselage section.

The digital photogrammetry image, in conjunction with the laser tracker measurements of the optical targets 20, allow a determination to be made as to the surface measurements in an X, Y, Z coordinate system of the fuselage section. In order to measure the entire outer surface 52 of the fuselage section 50, various portions of each fuselage section 50 can be measured separately. For example, in the case of a 24-foot-long fuselage section, the target projector 34 and two photogrammetry cameras 22a and 22b can be moved in 6-foot increments horizontally along the track 36, in order to record three more photogrammetry images in order to cover the entire length of the fuselage section 52.

In addition, by rotating the fuselage section 50 through a predetermined angle α predetermined number of times, the entire outer surface 52 of the fuselage section 50 may be measured. For example, the fuselage section 50 may be rotated a total of ten times in 36° increments in order to take a total of forty photogrammetry images of the entire outer surface 52 of the fuselage section 50. After, or during, each of the ten rotations of the fuselage section 50, the laser tracker 24 simultaneously measures the locations of the ten targets 28 distributed along the frame 27 in addition to the locations of optical target located at the forward and aft portions of the fuselage section 50. In this manner, measurements of the locations of each of the optical targets distributed around the entire outer surface of the fuselage section 50 can be determined utilizing laser tracking.

The photogrammetry and laser tracking measurements of the locations of the optical targets 20 can be integrated or merged utilizing one or more computers. In one embodiment, the location measurements in the X, Y, Z planes taken by the laser tracker 24 may be downloaded from a laser tracking computer to a photogrammetry computer, which combines the data into one or more combined measurements. The photogrammetry measurements are sometimes referred to as "point-cloud". A point cloud is a set of three-dimensional points describing the outlines or surface features of an object. The three-dimensional photogrammetry measurements may be transformed to conform to the laser tracking measurements to determine a more accurate, and/or more efficient combined measurement of the outer surface 52 of the fuselage section 50. One or more software programs may be utilized to create a three-dimensional computer-generated image of the outer surface 52 of the fuselage section 50. By utilizing photogrammetry and laser tracking devices concurrently, relatively quick and accurate measurements of the outer surface 52 may be made.

Figure 9:
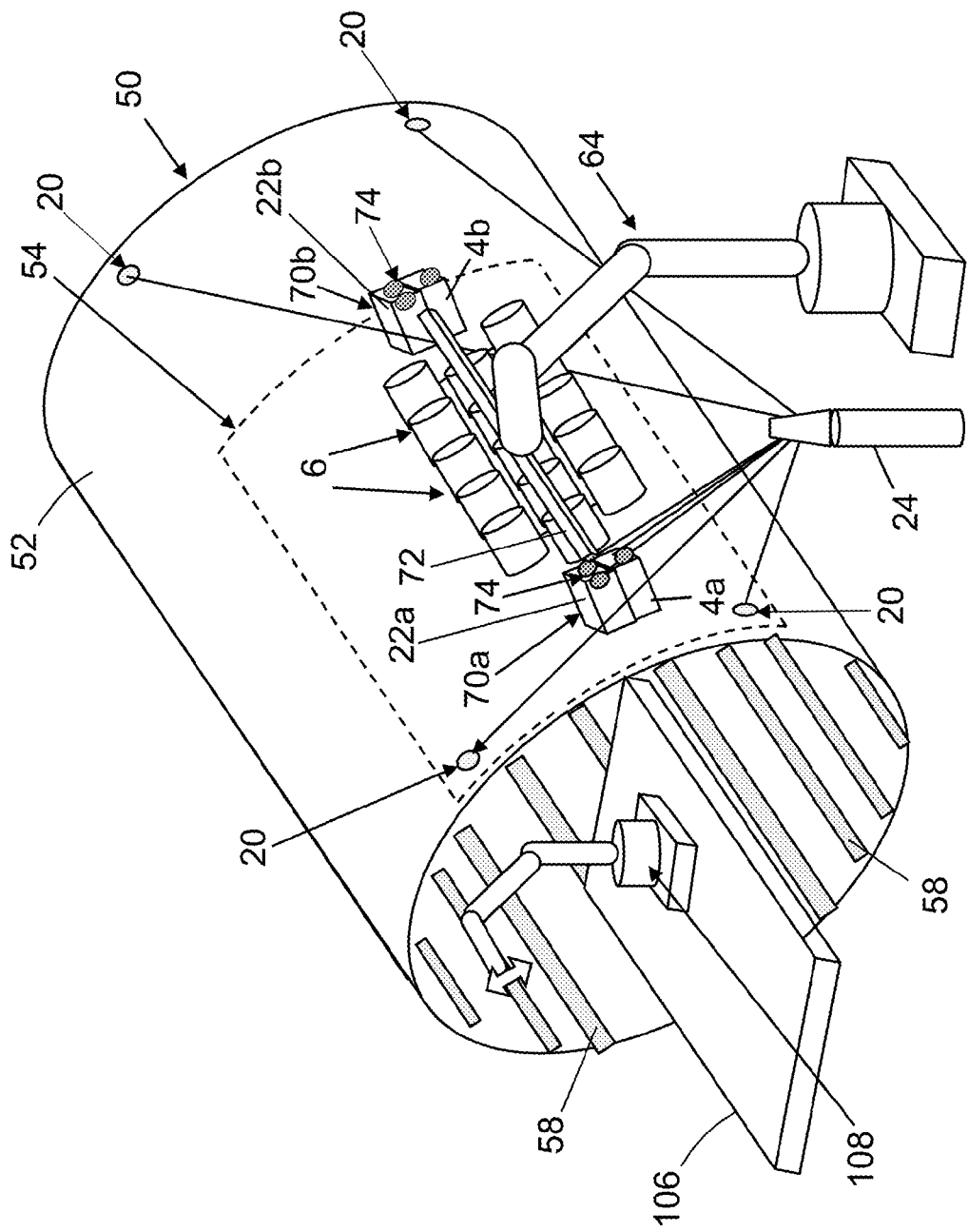
FIG. 9 is a diagram representing an isometric view of a full-barrel fuselage section being inspected by an automated non-destructive inspection system having two camera assemblies in accordance with a further embodiment. Each camera assembly comprises an infrared camera and a photogrammetry camera. A laser tracker determines the locations of the camera assemblies relative to the fuselage section using optical targets attached to the fuselage section and to the camera assemblies.

FIG. 9 is a diagram representing an isometric view of a full-barrel fuselage section 50 being inspected by an automated system having a camera assembly in accordance with a further embodiment. The camera assembly comprises first and second camera pairs 70a and 70b, each camera pair comprising a respective infrared camera attached to a respective photogrammetry camera. A laser tracker 24 and two photogrammetry cameras 22a and 22b can be used to determine the locations of two infrared cameras 4a and 4b relative to the fuselage section 50 using optical targets 20 attached to the fuselage section 50 and optical targets 74 attached to the camera pairs 70a and 70b.

The apparatus depicted in FIG. 9 comprises a robot 64 equipped to inspect the outer surface 52 of the fuselage section 50 using photogrammetry and infrared thermography. The robot 64 comprises a robot base and an articulated robotic arm similar to the robots previously described with reference to FIG. 2. A photogrammetric/infrared camera assembly is mounted to a distal end of the robotic arm of robot 64, e.g., by means of an end effector. In addition, the non-destructive inspection system depicted in FIG. 9 may also comprise a robot 108 movable on a platform 106 for ultrasonic inspection of stiffeners 58 attached to the internal surface of the fuselage section 50. An ultrasonic transducer array assembly is mounted to a distal end of the robotic arm of robot 108, e.g., by means of an end effector.

Still referring to FIG. 9, the robot 64 comprises a movable robot base and an extendible robotic arm having a proximal end coupled to the robot base. The photogrammetric/infrared camera assembly comprises a frame 72 mounted to a distal end of the robotic arm. Various pieces of equipment are attached to and supported by the frame 72, including a target projector (not shown), a bank of flash lamps 6, a first camera pair 70a comprising a first infrared camera 4a and a first photogrammetry camera 22a, and a second camera pair 70b comprising a second infrared camera 4b and a second photogrammetry camera 22b. The target projector and flash lamps 6 are disposed between the first and second camera pairs 70a and 70b.

The system depicted in FIG. 9 further comprises a laser tracker 24, a first set of at least three optical targets 74 attached to the first camera pair 70a, a second set of at least three optical targets 74 attached to the second camera pair 70b, and a computer system (not shown in FIG. 9) configured to perform the following operations: (a) merge infrared imaging data acquired by the infrared cameras 4a and 4b from a first inspection area to form first infrared imaging data; (b) merge infrared imaging data acquired by the infrared cameras 4a and 4b from a second inspection area adjacent the first inspection area to form second infrared imaging data; and (c) stitch the first and second infrared imaging data together based on at least location data acquired by the laser tracker 24 and photogrammetry data acquired by the first and second photogrammetry cameras 22a and 22b.

Figure 11A:
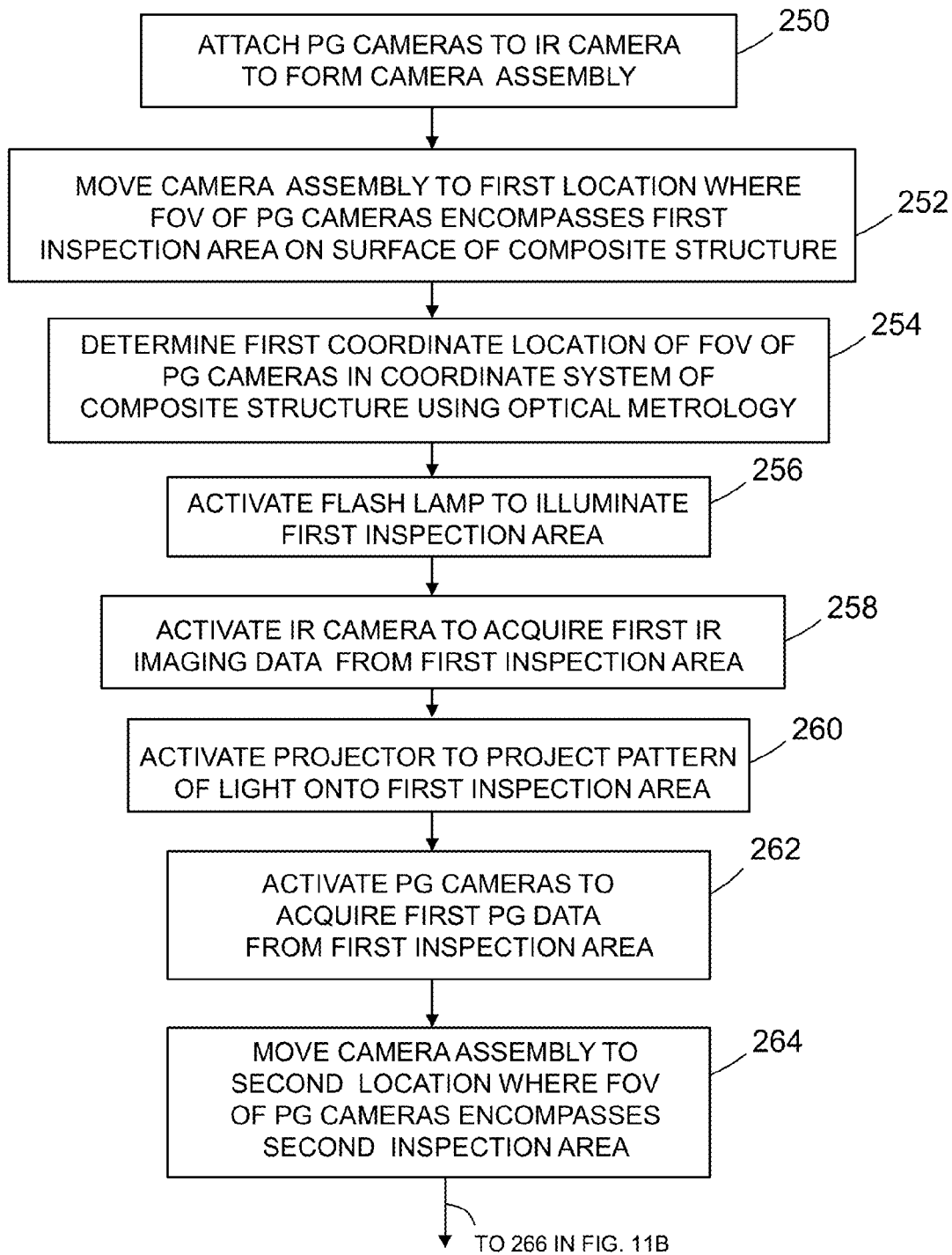
FIGS. 11A and 11B are respective parts of a flowchart identifying steps of a method for infrared thermographic inspection in accordance with further embodiments.
Figure 11B:
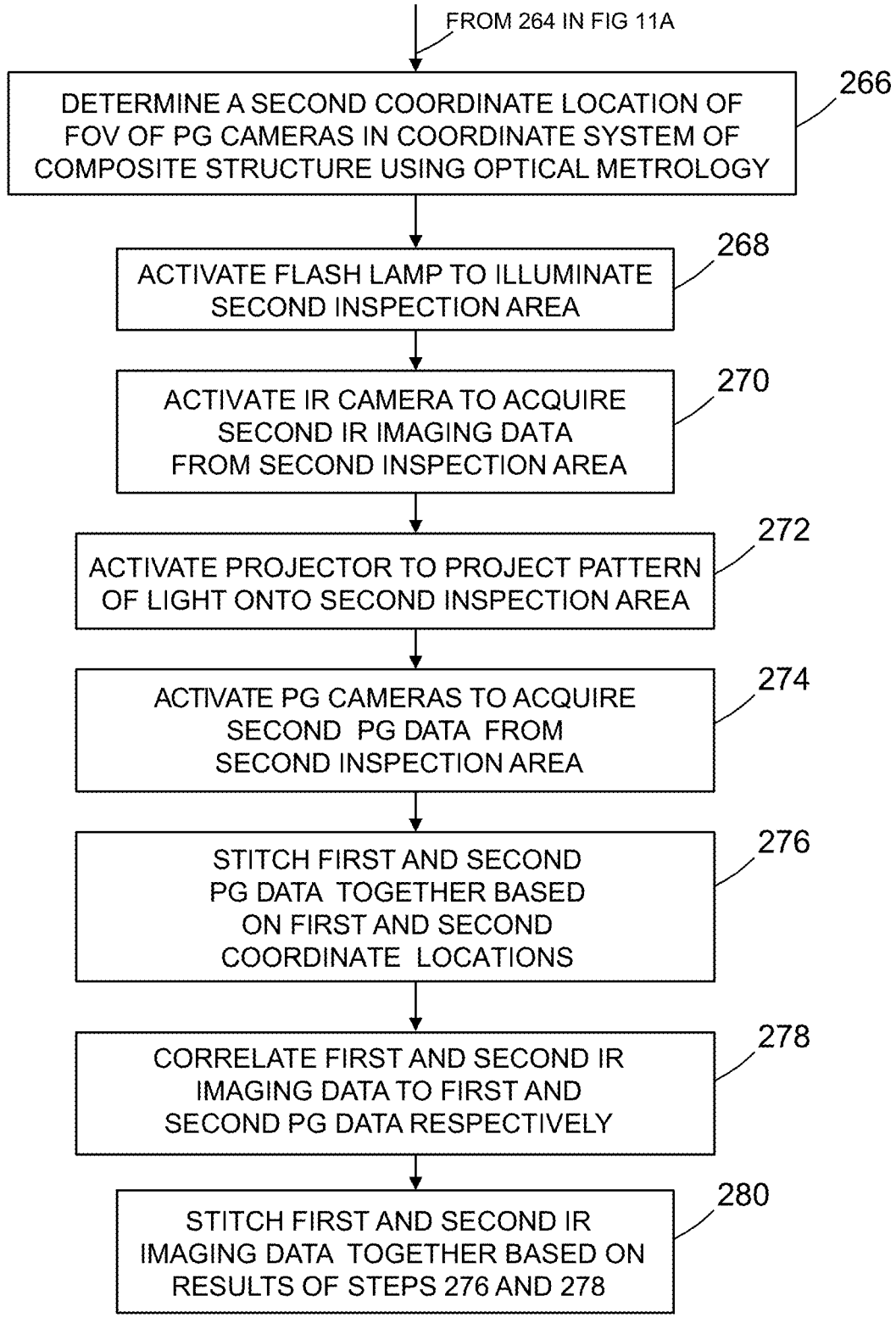

FIGS. 11A and 11B are respective parts of a flowchart identifying steps of a method for infrared thermographic inspection in accordance with the embodiment depicted in FIG. 9. Referring to FIG. 11A, the method comprises the following steps: (a) attaching two photogrammetry (PG) cameras 22a and 22b and two infrared (IR) cameras 4a and 4b in pairs to opposite ends of a frame to form a camera assembly (step 250); (b) moving the camera assembly to a first location whereat the combined field of view (FOV) of the photogrammetry cameras 22a and 22b encompass a first inspection area of a surface of the composite fuselage section 50 (step 252); (c) determining a first coordinate location of a field of view of the photogrammetry cameras 22a and 22b in a coordinate system of the composite fuselage section 50 using optical metrology while the camera assembly is at the first location (step 254); (d) activating at least one flash lamp 6 to output light that illuminates at least portions of the first inspection area (step 256); (e) activating the infrared cameras 4a and 4b to acquire first infrared imaging data while the combined field of view of the infrared cameras 4a and 4b encompasses at least the first inspection area (step 258); (f) activating a target projector 34 to project a pattern of light onto the first inspection area while the camera assembly is at the first location (step 260); (g) activating the photogrammetry cameras 22a and 22b to acquire first photogrammetry data while the combined field of view of the photogrammetry cameras 22a and 22b encompasses at least a portion of the projected pattern of light on the first inspection area (step 262); and (h) moving the camera assembly to a second location whereat the combined field of view of the photogrammetry cameras 22a and 22b encompasses a second inspection area of the surface of the composite fuselage section 50 (step 264).

Referring now to FIG. 11B, the method further comprises the following steps: (i) determining a second coordinate location of the combined field of view of the photogrammetry cameras 22a and 22b in the coordinate system of the composite fuselage section 50 using optical metrology while the camera assembly is at the second location (step 266); (j) activating at least one flash lamp 6 to output light that illuminates at least portions of the second inspection area (step 268); (j) activating the infrared cameras 4a and 4b to acquire second infrared imaging data while the combined field of view of the infrared cameras 4a and 4b encompasses at least the second inspection area (step 270); (k) activating the target projector 34 to project a pattern of light onto the second inspection area while the camera assembly is at the second location (step 272); (l) activating the photogrammetry cameras 22a and 22b to acquire second photogrammetry data while the combined field of view of the photogrammetry cameras 22a and 22b encompasses at least a portion of the projected pattern of light on the second inspection area (step 274); (m) stitching the first and second photogrammetry data together based on at least the first and second coordinate locations of the combined field of view of the photogrammetry cameras 22a and 22b in the coordinate system of the composite fuselage section 50 (step 276); (n) correlating the first and second infrared imaging data to the first and second photogrammetry data respectively (step 278); and (o) stitching the first and second infrared imaging data together based on at least the results of steps (m) and (n) (step 280).

Either of the non-destructive inspection systems depicted in FIGS. 2, 5 and 9 can be used to measure a number of characteristics including the porosity of a large-scale composite structure such as a fuselage section. Variations in the infrared imaging data acquired may be indicative of variations in the porosity (i.e., small internal voids) of the composite material. In accordance with a preferred embodiment, the thermographic porosity measurement process employs a standard thermal signature database comprising respective sets of standard thermal signatures acquired from composite material of different known thicknesses and different known porosities. In other words, for a specified thickness, the database comprises a respective data set representing different thermal signatures produced by different composite samples having that specified thickness but varying porosities. After first determining the thickness of the composite material at a specified point, the acquired thermal signature for that point is compared to the reference thermal signatures for that thickness. If a matching reference thermal signature is found, then the porosity percentage associated with that reference thermal signature in the thermal signature database is adopted as the thermographic porosity measurement for that specified point. In this manner the porosity percentages at all points in an inspection area can be determined using infrared thermography in a quick and efficient manner.

Figure 10:
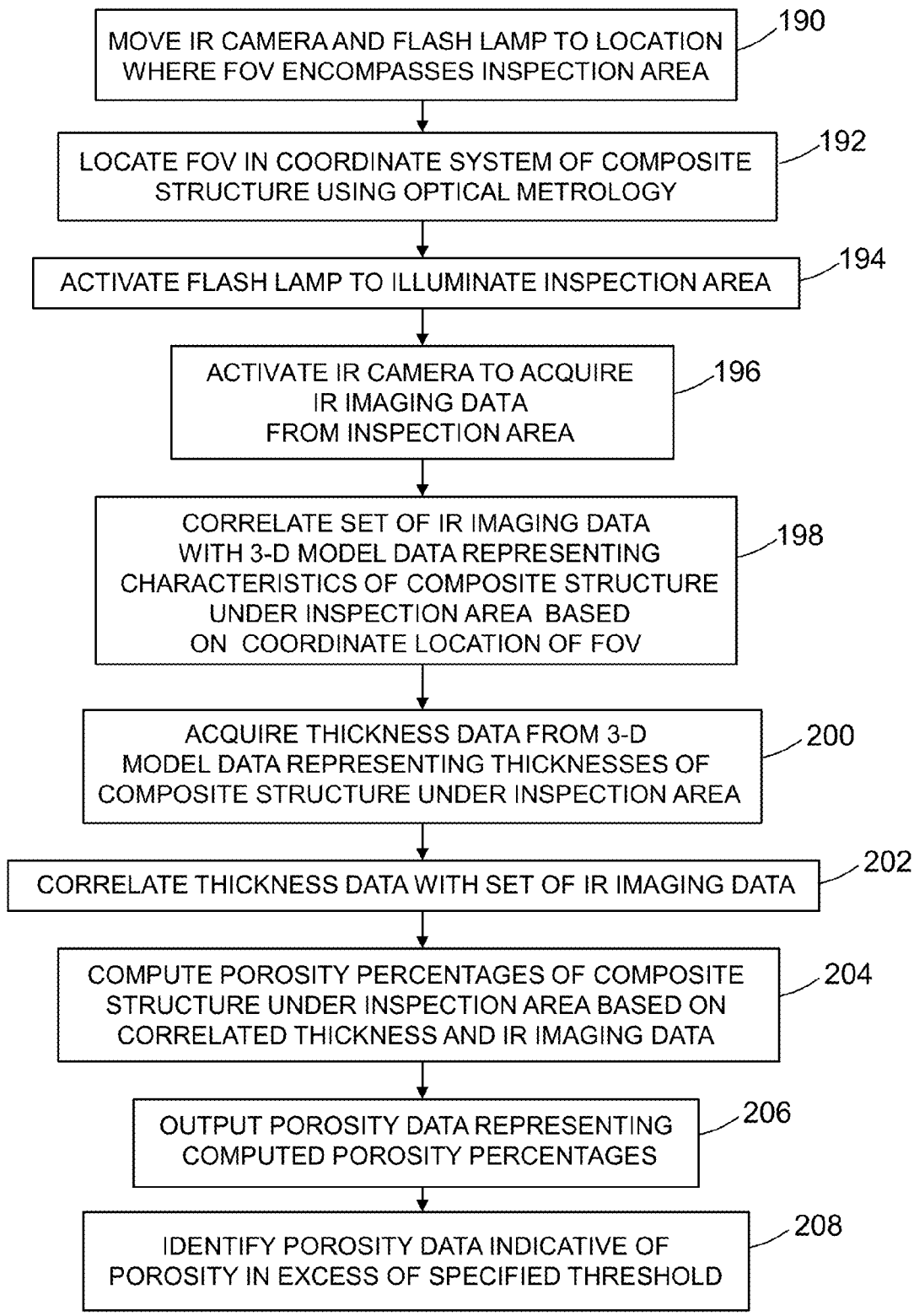
FIG. 10 is a flowchart identifying steps of a method for infrared thermographic inspection in accordance with other embodiments.

FIG. 10 is a flowchart identifying steps of a method for infrared thermographic measurement of the porosity of a composite structure in accordance with one embodiment. The method comprises: (a) moving an infrared (IR) camera 4 and at least one flash lamp 6 to a location at which a field of view (FOV) of the infrared camera 4 encompasses an inspection area of a surface of a composite structure (step 190); (b) locating the field of view of the infrared camera 4 in a coordinate system of the composite structure using optical metrology (step 192); (c) activating the at least one flash lamp 6 to output light that illuminates at least portions of the inspection area (step 194); (d) after step (c), activating the infrared camera 4 to acquire infrared imaging data while the field of view of the infrared camera 4 encompasses at least the inspection area (step 196); (e) correlating a set of the acquired infrared imaging data with three-dimensional model data representing characteristics of composite structure under the inspection area, the correlating being based on at least the location of the field of view of the infrared camera 4 in the coordinate system of the composite structure (step 198); (f) acquiring thickness data from the three-dimensional model data, the thickness data representing thicknesses of the composite structure under the inspection area (step 200); (g) correlating the acquired thickness data with the set of acquired infrared imaging data (step 202); (h)

computing porosity percentages of the composite structure under the inspection area based on at least the correlated thickness data and infrared imaging data (step 204); (i) outputting porosity data representing the computed porosity percentages; and (j) identifying porosity data indicative of porosity in excess of a specified threshold (step 208).

In accordance with some embodiments, step (h) in the previous paragraph comprises the following operations performed by a computer system: (i) selecting a data set from the reference thermal signature database, the data set representing a multiplicity of reference thermal signatures of a composite structure having the specified thickness and different respective porosity percentages; (ii) identifying a reference thermal signature of the multiplicity that best matches a subset of the set of acquired infrared imaging data corresponding to a coordinate position; (iii) retrieving from the reference thermal signature database porosity data associated with the identified thermal signature; and (iv) associating the retrieved porosity data with that coordinate position. By repeating this process for every coordinate position, porosity percentage data for the underlying composite structure can be mapped to the inspection area in the coordinate system of the composite structure.

With such mapped data for the composite structure, defect locations can subsequently be located and projected onto the composite structure after the scan, enabling an NDI expert or repair personnel to precisely find locations of anomalies and promptly proceed with disposition.

Figure 12:
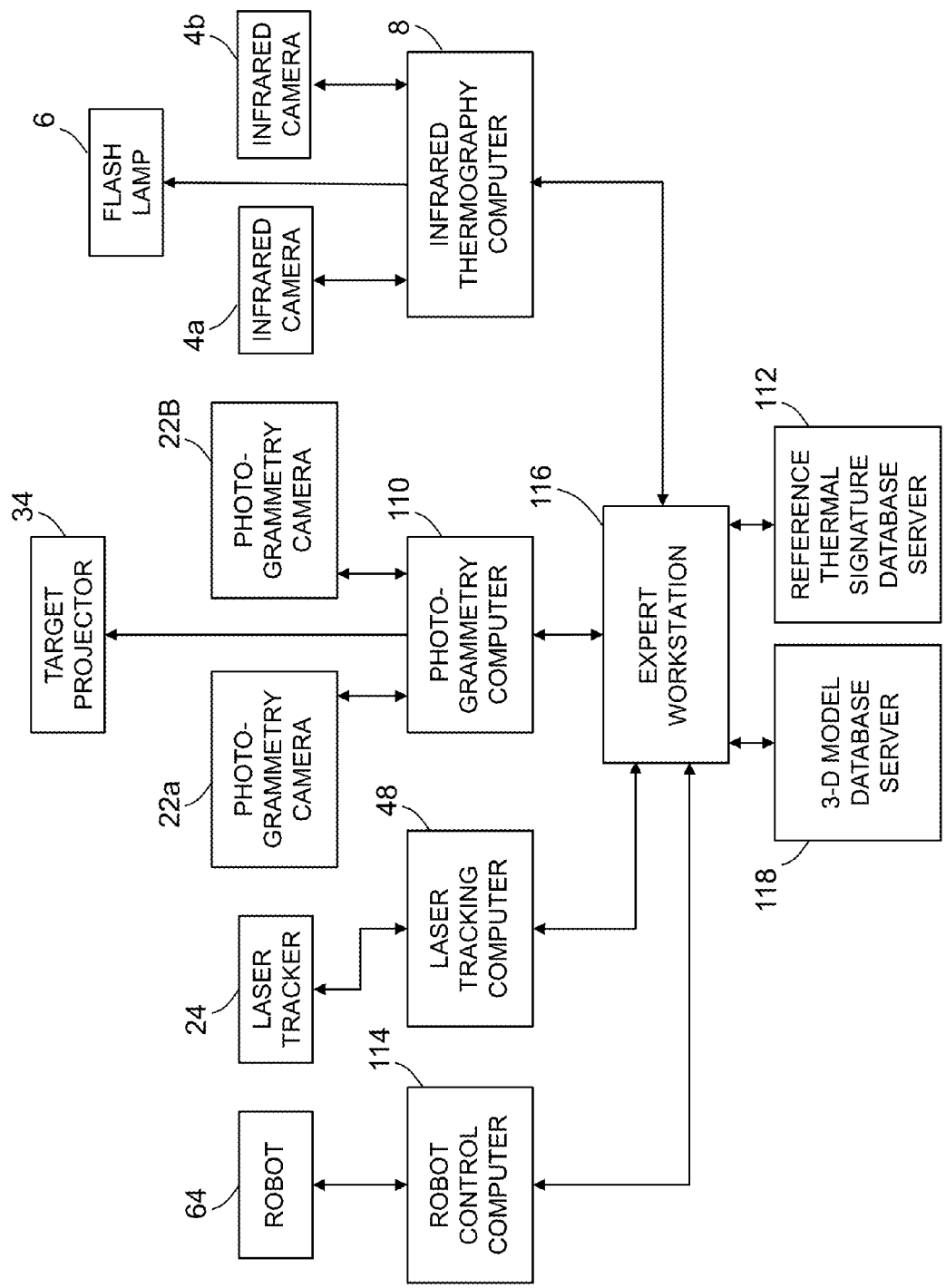
FIG. 12 is a block diagram identifying some components of a system for infrared thermographic inspection of large composite structures in accordance with some embodiments.

FIG. 12 is a block diagram identifying some components of a system for infrared thermographic inspection of large-scale composite structures in accordance with one computer architecture. Movements of a robot 64 are controlled by a robot control computer 114. Movements and firing of the laser tracker 24 are controlled by a laser tracking computer 48, which also receives laser tracking data from the laser tracker 24. Activation of the target projector 34 and activation of the photogrammetry cameras 22a and 22b are controlled by a photogrammetry computer 110, which also receives photogrammetry data from the photogrammetry cameras 22a and 22b. Activation of the flash lamps 6 and activation of the infrared cameras 4a and 4b are controlled by an infrared thermography computer 8, which also receives infrared imaging data from the infrared cameras 4a and 4b. All of these computers can be in wireline or wireless communication with a master computer at an expert workstation 116. The master computer at the expert workstation 116 may be programmed to correlate the laser tracking data with the infrared imaging data, to correlate the laser tracking data with the photogrammetry data, and to correlate the photogrammetry data with the infrared imaging data. The master computer may be further programmed to request 3-D model data from a 3-D model database server 118. In the case of thermographic porosity measurement, the master computer at the expert workstation 116 may also be programmed to request reference thermal signature data from a reference thermal signature database server 112.

The laser tracking computer 48 acquires location data for the photogrammetry cameras 22a and 22b and/or infrared cameras 4a and 4b in a 3-D coordinate system of the composite structure. In the case of a barrel-shaped fuselage section, the photogrammetry data and/or infrared imaging data can be mapped directly onto a 3-D model of the fuselage section. The overlay of photogrammetry data and/or infrared imaging data with the 3-D model data enables improved data analysis and potential automated data analysis as well. For example, features/flaw indications can be directly correlated to the fuselage structure by direct overlay of infrared imaging data on the 3-D model. In addition, the direct data overlay onto the model can be used to determine the thickness of a local area or spatial point, which is needed for porosity quantification. In one embodiment, the process involves application of infrared imaging data strips as one or more computer graphics texture maps, which are projected onto the 3-D model surfaces in a virtual environment displayed on a monitor or computer screen at the expert workstation 116.

Configured correctly, infrared thermography can be done very rapidly over large areas, without couplant and without touching the part. Current ultrasonic scan times are about 4 seconds per square foot for ultrasonic transducer arrays on a robot. For example, a 4-inch ultrasonic transducer array traveling at 9 inches per second would cover 2.5 square feet in 10 seconds. Depending on the resolution required and the thickness of the composite part, a 2-foot×2-foot infrared flash hood could collect imaging data from 4 square feet in 10 seconds. That is 2.5 seconds per square foot. That is an inspection time reduction of almost 40 percent. A 3-foot× 3-foot infrared flash hood could collect imaging data from 9 square feet in 10 seconds, which translates to 1.1 seconds per square foot, or almost 4 times faster than ultrasonic transducer array scanning of the same area.

Figure 13:
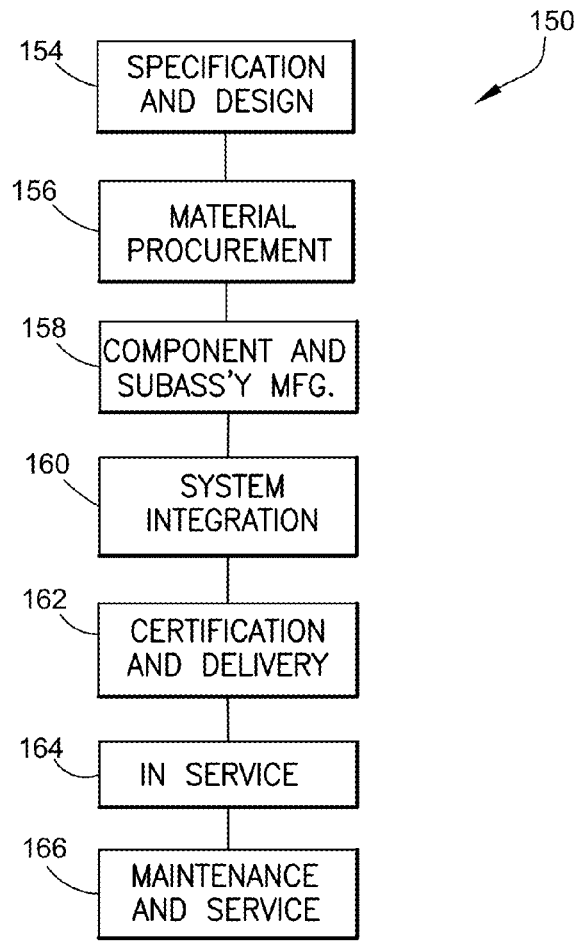
FIG. 13 is a flow diagram of an aircraft production and service methodology.
Figure 14:
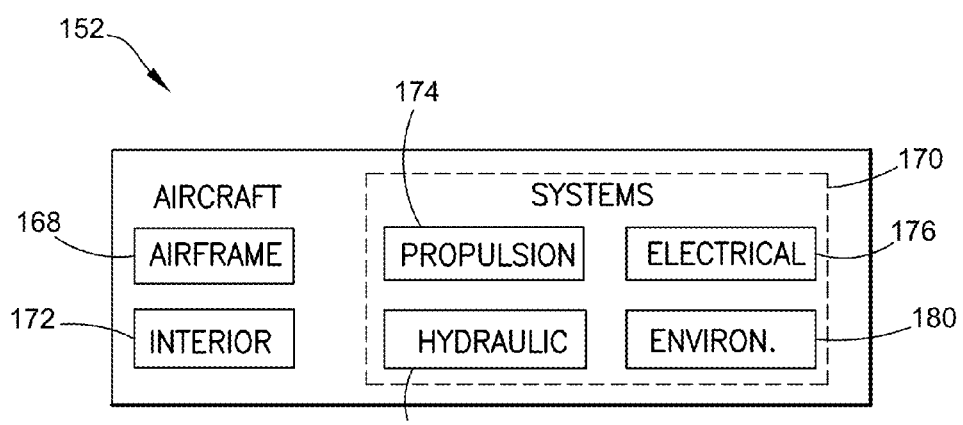
FIG. 14 is a block diagram showing systems of an aircraft.

The systems and methods disclosed above may be employed in an aircraft manufacturing and service method 150 as shown in FIG. 13 for inspecting parts of an aircraft 152 as shown in FIG. 14. During pre-production, exemplary method 150 may include specification and design 154 of the aircraft 152 and material procurement 156. During production, component and subassembly manufacturing 158 and system integration 160 of the aircraft 152 takes place. Thereafter, the aircraft 152 may go through certification and delivery 162 in order to be placed in service 164. While in service by a customer, the aircraft 152 is scheduled for routine maintenance and service 166 (which may also include modification, reconfiguration, refurbishment, and so on).

Each of the processes of method 150 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 14, the aircraft 152 produced by exemplary method 150 may include an airframe 168 (comprising, e.g., a fuselage, frames, stiffeners, wing boxes, etc.) with a plurality of systems 170 and an interior 172. Examples of high-level systems 170 include one or more of the following: a propulsion system 174, an electrical system 176, a hydraulic system 178, and an environmental control system 180. Any number of other systems may be included. Although an aerospace example is shown, the principles disclosed herein may be applied to other industries, such as the automotive industry.

Apparatus and methods embodied herein may be employed during any one or more of the stages of the production and service method 150. For example, components or subassemblies fabricated or assembled during production process 158 may be inspected using the infrared thermographic inspection system disclosed herein. Also, one or more apparatus embodiments, method embodiments, or a combination thereof may be utilized during the production stages 158 and 160, for example, by substantially expediting nondestructive inspection of or reducing the cost of an aircraft 152. Similarly, one or more of apparatus embodiments, method embodiments, or a combination thereof may be utilized while the aircraft 152 is in service, for example and without limitation, during maintenance and service 166.

While infrared thermographic inspection systems have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising at least one processing unit (e.g., a central processing unit, an integrated circuit or an arithmetic logic unit).

As used in the claims, the term "location" comprises position in a fixed three-dimensional coordinate system and orientation relative to that coordinate system.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude two or more steps or portions thereof being performed concurrently or to exclude any portions of two or more steps being performed alternatingly.

The invention claimed is:

1. A method for infrared thermographic inspection of a composite structure comprising:
   (a) moving an infrared camera to a first location whereat a field of view of the infrared camera encompasses a first inspection area of a surface of the composite structure;
   (b) determining a first coordinate location of the field of view of the infrared camera in a coordinate system of the composite structure using optical metrology while the infrared camera is at the first location;
   (c) activating at least one flash lamp to output light that illuminates at least portions of the first inspection area;
   (d) activating the infrared camera to acquire first infrared imaging data while the field of view of the infrared camera encompasses at least the first inspection area;
   (e) moving the infrared camera to a second location whereat the field of view of the infrared camera encompasses a second inspection area of the surface of the composite structure;
   (f) determining a second coordinate location of the field of view of the infrared camera in the coordinate system of the composite structure using optical metrology while the infrared camera is at the second location;
   (g) activating at least one flash lamp to output light that illuminates at least portions of the second inspection area;
   (h) activating the infrared camera to acquire second infrared imaging data while the field of view of the infrared camera encompasses at least the second inspection area; and
   (i) stitching the first and second infrared imaging data together based on at least the first and second coordinate locations of the field of view of the infrared camera in the coordinate system of the composite structure.

2. The method as recited in claim 1, wherein said optical metrology comprises laser tracking.

3. The method as recited in claim 2, wherein steps (b) and (f) collectively comprise:
   placing optical targets on the composite structure;
   directing respective pulses of light from a laser tracker toward the optical targets on the composite structure;
   processing light returned from the optical targets on the composite structure to the laser tracker to determine first location data representing a coordinate location of the composite structure in a coordinate system of the laser tracker;
   placing optical targets on a robot base that supports a robotic arm which supports the infrared camera;
   directing respective pulses of light from the laser tracker toward the optical targets on the robot base;
   processing light returned from the optical targets on the robot base to the laser tracker to determine second location data representing a coordinate location of the robot base in the coordinate system of the laser tracker;
   encoding movements of the robotic arm; and
   computing the first and second coordinate locations of the field of view of the infrared camera in the coordinate system of the composite structure based on at least the first and second location data and encoded movements of the robotic arm.

4. The method as recited in claim 2, wherein steps (b) and (f) collectively comprise:
   placing optical targets on the composite structure;
   directing respective pulses of light from one or more laser trackers toward the optical targets on the composite structure;
   processing light returned from the optical targets on the composite structure to determine first location data representing a coordinate location of the composite structure in a coordinate system of the one or more laser trackers;
   attaching respective sets of optical targets to first, second and third bars;
   placing the first, second and third bars adjacent the composite structure in respective locations so that the first and second bars are separated by the first inspection area, and the second and third bars are separated by the second inspection area;
   directing respective pulses of light from the one or more laser trackers toward the optical targets on the first and second bars during activations of the infrared camera in step (d);
   directing respective pulses of light from the one or more laser trackers toward the optical targets on the second and third bars during activations of the infrared camera in step (h);
   processing light returned from the optical targets on the first, second and third bars to determine second location data representing respective coordinate locations of the first, second and third bars in the coordinate system of the one or more laser trackers; and
   computing the first and second coordinate locations of the field of view of the infrared camera in the coordinate system of the composite structure based on at least the first and second location data and the first and second infrared imaging data.

5. The method as recited in claim 4, wherein computing the first and second coordinate locations of the field of view of the infrared camera in the coordinate system of the composite structure comprises identifying portions of the first infrared imaging data which correspond to light returned from the optical targets on the first and second bars.

6. The method as recited in claim 1, wherein said optical metrology comprises photogrammetry.

7. A method for infrared thermographic inspection comprising:
 (a) attaching a pair of photogrammetry cameras to an infrared camera to form a camera assembly;
 (b) moving the camera assembly to a first location whereat respective fields of view of the photogrammetry cameras encompass a first inspection area of a surface of the composite structure;
 (c) determining a first coordinate location of a field of view of the photogrammetry cameras in a coordinate system of the composite structure using optical metrology while the camera assembly is at the first location;
 (d) activating at least one flash lamp to output light that illuminates at least portions of the first inspection area;
 (e) activating the infrared camera to acquire first infrared imaging data while the field of view of the infrared camera encompasses at least the first inspection area;
 (f) activating a projector to project a pattern of light onto the first inspection area while the camera assembly is at the first location;
 (g) activating the photogrammetry cameras to acquire first photogrammetry data while the field of view of the photogrammetry cameras encompasses at least a portion of the projected pattern of light on the first inspection area;
 (h) moving the camera assembly to a second location whereat the field of view of the photogrammetry cameras encompasses a second inspection area of the surface of the composite structure;
 (i) determining a second coordinate location of the field of view of the photogrammetry cameras in the coordinate system of the composite structure using optical metrology while the camera assembly is at the second location;
 (j) activating at least one flash lamp to output light that illuminates at least portions of the second inspection area;
 (j) activating the infrared camera to acquire second infrared imaging data while the field of view of the infrared camera encompasses at least the second inspection area;
 (k) activating a projector to project a pattern of light onto the second inspection area while the camera assembly is at the second location;
 (l) activating the photogrammetry cameras to acquire second photogrammetry data while the field of view of the photogrammetry cameras encompasses at least a portion of the projected pattern of light on the second inspection area;
 (m) stitching the first and second photogrammetry data together based on at least the first and second coordinate locations of the field of view of the photogrammetry cameras in the coordinate system of the composite structure;
 (n) correlating the first and second infrared imaging data to the first and second photogrammetry data respectively; and
 (o) stitching the first and second infrared imaging data together based on at least the results of steps (m) and (n).

8. The method as recited in claim 7, wherein said optical metrology comprises laser tracking.

9. The method as recited in claim 8, wherein steps (c) and (i) collectively comprise:
 placing optical targets on the composite structure;
 directing respective pulses of light from a laser tracker toward the optical targets on the composite structure;
 processing light returned from the optical targets on the composite structure to the laser tracker to determine first location data representing a coordinate location of the composite structure in a coordinate system of the laser tracker;
 placing optical targets on the camera assembly;
 directing respective pulses of light from the laser tracker toward the optical targets on the camera assembly;
 processing light returned from the optical targets on the camera assembly to the laser tracker to determine second location data representing a coordinate location of the field of view of the photogrammetry cameras in the coordinate system of the laser tracker; and
 computing the first and second coordinate locations of the field of view of the photogrammetry cameras in the coordinate system of the composite structure based on at least the first and second location data.

10. The method as recited in claim 9, wherein computing the first coordinate location of the field of view of the photogrammetry cameras in the coordinate system of the composite structure comprises identifying portions of the first photogrammetry data which correspond to light returned from optical targets on the composite structure.

11. The method as recited in claim 7, wherein said optical metrology comprises photogrammetry.

12. A system for infrared thermographic inspection of a workpiece, comprising:
 a robot comprising a movable robot base and an extendible robotic arm having a proximal end coupled to said robot base;
 a frame mounted to a distal end of said robotic arm;
 a target projector mounted to said frame and configured to project dot patterns of light onto the workpiece;
 a laser tracker;
 a flash lamp mounted to said frame;
 a camera assembly mounted to said frame, said camera assembly comprising first and second camera pairs, said first camera pair comprising a first infrared camera and a first photogrammetry camera, and said second camera pair comprising a second infrared camera and a second photogrammetry camera, wherein said target projector and said flash lamp are disposed between said first and second camera pairs;
 a first multiplicity of optical targets attached to the workpiece;
 a second multiplicity of optical targets attached to either said robot or said camera assembly; and
 a computer system configured to stitch first and second infrared imaging data acquired by said infrared camera based on at least location data acquired from said first and second multiplicities of optical targets by said laser tracker and photogrammetry data acquired by said first and second photogrammetry cameras.

13. The system as recited in claim 12, wherein said second multiplicity of optical targets are attached to said robot base.

14. The system as recited in claim 12, wherein said second multiplicity of optical targets comprise a first set of at least three optical targets attached to said first camera pair and a second set of at least three optical targets attached to said second camera pair.

15. A system for infrared thermographic inspection of a workpiece, comprising:
   a robot comprising a movable robot base and an extendible robotic arm having a proximal end coupled to said robot base;
   a frame mounted to a distal end of said robotic arm;
   a target projector mounted to said frame and configured to project dot patterns of light onto the workpiece;
   a laser tracker;
   a plurality of vertical bars spaced between the workpiece and the laser tracker;
   a flash lamp mounted to said frame;
   a camera assembly mounted to said frame, said camera assembly comprising first and second camera pairs, said first camera pair comprising a first infrared camera and a first photogrammetry camera, and said second camera pair comprising a second infrared camera and a second photogrammetry camera, wherein said target projector and said flash lamp are disposed between said first and second camera pairs;
   a first multiplicity of optical targets attached to the workpiece;
   a second multiplicity of optical targets attached to said vertical bars; and
   a computer system configured to stitch first and second infrared imaging data acquired by said infrared camera based on at least location data acquired from said first and second multiplicities of optical targets by said laser tracker and photogrammetry data acquired by said first and second photogrammetry cameras.

* * * * *